(12) United States Patent
Hitoshi et al.

(10) Patent No.: US 7,358,040 B2
(45) Date of Patent: Apr. 15, 2008

(54) MRE 11: MODULATION OF CELLULAR PROLIFERATION

(75) Inventors: Yasumichi Hitoshi, Mountain View, CA (US); Susan Demo, Sunnyvale, CA (US); Yonchu Jenkins, San Francisco, CA (US)

(73) Assignee: Rigel Pharmaceuticals, Incorporated, South San Francisco, CA (US)

( * ) Notice: Subject to any disclaimer, the term of this patent is extended or adjusted under 35 U.S.C. 154(b) by 744 days.

(21) Appl. No.: 10/026,331

(22) Filed: Dec. 21, 2001

(65) Prior Publication Data

US 2003/0027167 A1    Feb. 6, 2003

Related U.S. Application Data

(60) Provisional application No. 60/309,737, filed on Aug. 1, 2001.

(51) Int. Cl.
*C12Q 1/00* (2006.01)

(52) U.S. Cl. .......................................... 435/4

(58) Field of Classification Search .................... 435/5, 435/6, 701; 436/94, 500; 536/24.5; 530/300, 530/350
See application file for complete search history.

(56) References Cited

U.S. PATENT DOCUMENTS

2002/0115057 A1* 8/2002 Young .......................... 435/4
2002/0182586 A1* 12/2002 Morris et al. .................. 435/4

OTHER PUBLICATIONS de Jager et al. Nuc. Acids Res. 2001; 29:1317-25.*
Furuse et al. EMBO J. 1998.*
Lanson et al. Nuc. Acids Res. 2000; 28:2882-92.*
Moreau et al. Mol. Cell. Biol. 1999; 19:556-566.*
Paull et al. Genes Dev. 1999; 13:1276-88.*
Petrini, Am. J. Hum. Genet. 1999; 64:1264-69.*
Fukuda, T. et al. "Alterations of the Double-strand Break Repair Gene MRE11 in Cancer," *Cancer Res.*, Jan. 1, 2001, pp. 23-26, vol. 61.
Hopfner, K. et al. "Structural Biochemistry and Interaction Architecture of the DNA Double-strand Break Repair MRE11 Nuclease and RAD50-ATPase," *Cell*, May 18, 2001, pp. 473-485, vol. 105.
Kim, K. K. et al. "Mouse RAD50 has Limited Epitopic Homology to p53 and is Expressed in the Adult Myocardium," *J. Biol., Chem.* Nov. 15, 1996, pp. 29255-29264, vol. 271, No. 46.
Lombard, D. B. and Guarente, L. "Nijmegen Breakage Syndrome Disease Protein and MRE11 at PML Nuclear Bodies and Meiotic Telomeres," *Cancer Res.*, May 1, 2000, pp. 2331-2334, vol. 60.
Paull, T. T. and Gellert, M. "The 3' to 5' Exonuclease Activity of MRE11 Facilities Repair of DNA Double-strand Breaks," *Molecular Cell*, Jun. 1998, pp. 969-979, vol. 1.
Petrini, J. H. L. "DNA Repair '99: The Mammalian MRE11-RAD50-NBS1 Protein Complex: Integration of Functions in the Cellular DNA-Damage Response," *Am. J. Hum. Genet.*, 1999, pp. 1264-1269, vol. 64.
Stewart, G. S. et al. "The DNA Double-Strand Break Repair Gene hMRE11 is Mutated in Individuals with an Ataxia-Telangiectasia-like Order," *Cell*, Dec. 10, 1999, pp. 577-587, vol. 99.

* cited by examiner

*Primary Examiner*—Nancy Vogel
(74) *Attorney, Agent, or Firm*—Townsend & Townsend & Crew LLP

(57) ABSTRACT

The present invention relates to regulation of cellular proliferation. More particularly, the present invention is directed to nucleic acids encoding MRE11, which is a protein involved in modulation of cellular proliferation. The invention further relates to methods for identifying and using agents, including small molecule chemical compositions, antibodies, peptides, cyclic peptides, nucleic acids, antisense nucleic acids, and ribozymes, that modulate cellular proliferation via modulation of MRE11; as well as to the use of expression profiles and compositions in diagnosis and therapy related to modulation of cellular proliferation.

22 Claims, 36 Drawing Sheets

Figure 1

SEQ ID NO:1

```
   1 ccacgcgtcc gggacgccgt tctctcccgc ggaattcagg tttacggccc tgcgggttct
  61 cagagaattt ctagaatttg gaatcgagtg cattttctga catttgagta cagtacccag
 121 gggttcttgg agaagaacct ggtcccagag gagcttgact gaccataaaa atgagtactg
 181 cagatgcact tgatgatgaa aacacattta aaatattagt tgcaacagat attcatcttg
 241 gatttatgga gaaagatgca gtcagaggaa atgatacgtt tgtaacactc gatgaaattt
 301 taagacttgc ccaggaaaat gaagtggatt ttatttttgtt aggtggtgat cttttttcatg
 361 aaaataagcc ctcaaggaaa acattacata cctgcctcga gttattaaga aaatattgta
 421 tgggtgatcg gcctgtccag tttgaaattc tcagtgatca gtcagtcaac tttggttttta
 481 gtaagtttcc atgggtgaac tatcaagatg caacctcaa catttcaatt ccagtgttta
 541 gtattcatgg caatcatgac gatcccacag gggcagatgc actttgtgcc ttggacattt
 601 taagttgtgc tggatttgta aatcactttg gacgttcaat gtctgtggag aagatagaca
 661 ttagtccggt tttgcttcaa aaaggaagca caaagattgc gctatatggt ttaggatcca
 721 ttccagatga aggctctat cgaatgtttg tcaataaaaa agtaacaatg ttgagaccaa
 781 aggaagatga gaactcttgg tttaacttat ttgtgattca tcagaacagg agtaaacatg
 841 gaagtactaa cttcattcca gaacaatttt tggatgactt cattgatctt gttatctggg
 901 gccatgaaca tgagtgtaaa atagctccaa ccaaaaatga acaacagctg ttttatatct
 961 cacaacctgg aagctcagtg gttacttctc tttccccagg agaagctgta aagaaacatg
1021 ttggtttgct gcgtattaaa gggaggaaga tgaatatgca taaaattcct cttcacacag
1081 tgcggcagtt tttcatggag gatattgttc tagctaatca tccagacatt tttaacccag
1141 ataatcctaa agtaacccaa gccatacaaa gcttctgttt ggagaagatt gaagaaatgc
1201 ttgaaaatgc tgaacgggaa cgtctgggta attctcacca gccagagaag cctcttgtac
1261 gactgcgagt ggactatagt ggaggttttg aacctttcag tgttcttcgc tttagccaga
1321 aatttgtgga tcgggtagct aatccaaaag acattatcca tttttttcagg catagagaac
1381 aaaaggaaaa aacaggagaa gagatcaact ttgggaaact tatcacaaag ccttcagaag
1441 gaacaacttt aagggtagaa gatcttgtaa aacagtactt tcaaaccgca gagaagaatg
1501 tgcagctctc actgctaaca gaaagaggga tgggtgaagc agtacaagaa tttgtggaca
1561 aggaggagaa agatgccatt gaggaattag tgaaatacca gttggaaaaa acacagcgat
1621 ttcttaaaga acgtcatatt gatgccctcg aagacaaaat cgatgaggag gtacgtcgtt
1681 tcagagaaac cagacaaaaa aatactaatg aagaagatga tgaagtccgt gaggctatga
1741 ccagggccag agcactcaga tctcagtcag aggagtctgc ttctgccttt agtgctgatg
1801 accttatgag tatagattta gcagaacaga tggctaatga ctctgatgat agcatctcag
1861 cagcaaccaa caaaggaaga ggccgaggaa gaggtcgaag aggtggaaga gggcagaatt
1921 cagcatcgag aggagggtct caaagaggaa gagcagacac tggtctggag acttctaccc
1981 gtagcaggaa ctcaaagact gctgtgtcag catctagaaa tatgtctatt atagatgcct
2041 ttaaatctac aagacagcag ccttcccgaa atgtcactac taagaattat tcagaggtga
2101 tgaggtaga tgaatcagat gtggaagaag acatttttcc taccacttca aagacagatc
2161 aaaggtggtc cagcacatca tccagcaaaa tcatgtccca gagtcaagta tcgaaagggg
2221 ttgattttga atcaagtgag gatgatgatg atgatccttt tatgaacact agttctttaa
2281 gaagaaatag aagataatat atttaatggc actgagaaac atgcaagata caggaaaaat
2341 gaaaatgtta caagctaaga gttacagtt taagatttta agtattgttc cctgagcata
2401 actccataag taagaaattt ctagttcaca gacatacaat agcattgatt caccttgttt
2461 ttttaacctg gttgttgtag taagagcttt gtttcaatat cactcttgag taaagattaa
2521 aataaagcta ccatttt
```

Figure 2

SEQ ID NO:2

```
  1 mstadaldde ntfkilvatd ihlgfmekda vrgndtfvtl deilrlaqen evdfillggd
 61 lfhenkpsrk tlhtclellr kycmgdrpvq feilsdqsvn fgfskfpwvn yqdgnlnisi
121 pvfsihgnhd dptgadalca ldilscagfv nhfgrsmsve kidispvllq kgstkialyg
181 lgsipderly rmfvnkkvtm lrpkedensw fnlfvihqnr skhgstnfip eqflddfidl
241 viwgheheck iaptkneqql fyisqpgssv vtslspgeav kkhvgllrik grkmnmhkip
301 lhtvrqffme divlanhpdi fnpdnpkvtq aiqsfcleki eemlenaere rlgnshqpek
361 plvrlrvdys ggfepfsvlr fsqkfvdrva npkdiihffr hreqkektge einfgklitk
421 psegttlrve dlvkqyfqta eknvqlslt ergmgeavqe fvdkeekdai eelvkyqlek
481 tqrflkerhi daledkidee vrrfretrqk ntneeddevr eamtraralr sqseesasaf
541 saddlmsidl aeqmandsdd sisaatnkgr grgrgrrggr gqnsasrggs qrgradtgle
601 tstrsrnskt avsasrnmsi idafkstrqq psrnvttkny sevievdesd veedifptts
661 ktdqrwssts sskimsqsqv skgvdfesse dddddpfmnt sslrrnrr
```

Dominant Negative Mutants Generated for Target

Validation Studies

Two inactivating mutants were generated analogous to catalytically inactivating mutations in the yeast MRE11:

H217Y (MCB 1998 Jan;18(1):260-68)
H129N (MCB 1999 Jan;19(1):556-66)

Both histidines are thought to form part of the $Mn^{2+}$ coordination site (7 histidines coordinate 2 $Mn^{2+}$ ions) in the catalytic core of the protein. H129 is predicted to act in transition state stabilization by donating a proton to the leaving DNA 3'-OH during the cleavage of the sugar 3'-O-phosphate bond of DNA

```
hMRE11    9   DENTFKILVATDIHLGFMEKDAARGNDTFVTLDEILRLAQENEVDFILLG GDLFHENKPS    68
              D +T +IL+ TD H+G+ E D   G+D++ T   E++ LA+ N VD ++   GDLFH NKPS
SCMRE11   5   DPDTIRILITTDNHVGYNENDPITGDDSWKTFHEVMLAKNNNVDMVVQSGDLFHVNKPS    64

69  RKTLHTCLELLRKYCMGDRPVQFEILSDQSVNFGFSKFPWVNYQDGNLNISIPVFSIHGN   128
              +K+L+   L+ LR  CMGD+P + E+LSD  S   F + +F  VNY+D N NI SIPVF I GN
          65  KKSLYQVLKTLRLCCMGDKPCELELLSDPSQVFHYDEFTNVNYEDPNFNISIPVFGISGN   124
              *

129  HDDPTGADALCALDILSCAGFVNHFGRSMSVEKIDISPVLLQKGSTKIALYGLGSIPDER   188
              HDD +G   LC  +DIL   G +NHFG+ +   +KI + P+L QKGSTK+ALYGL ++ DER
         125  HDDASGDSLLCPMDILHATGLINHFGKVIESDKIKVVPLLFQKGSTKLALYGLAAVRDER   184

189  LYRMFVNKKVTMLRPKEDENSWFNLFVI HQNRSKHGSTNFIPEQFLDDFIDLVIWGHEHE   248
              L+R F +  VT   P   E  WFNL  +HQN + H  +T F+PEQFL DF+D+VIWGHEHE
         185  LFRTFKDGGVTFEVPTMREGEWFNLMCV HQNHTGHTNTAFLPEQFLPDFLDMVIWGHEHE   244

249  CKIAPTKNEQQLFYISQPGSSVVTSLSPGEAVKKHVGLLRIK -GRKMNMHKIPLHTVRQF   307
              C    N  + F + QPGSSV TSL    EA  K+V +L IK G    M  IPL T+R F
         245  CIPNLVHNPIKNFDVLQPGSSVATSLCEAEAQPKYVFILDIKYGEAPKMTPIPLETIRTF   304
```

FIG. 4

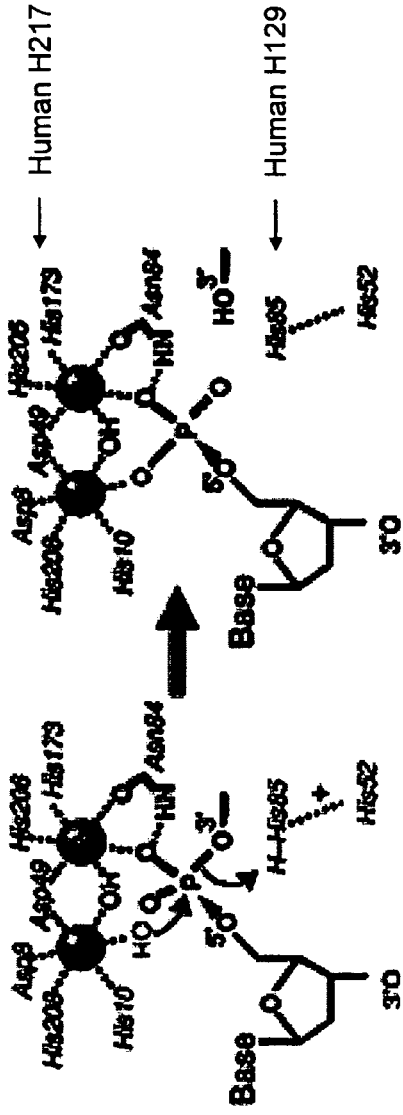

Representation of Active Site of P. furiosus Mre11

$Mn^{2+}$ coordination site  7 histidines coordinate 2 $Mn^{2+}$ ions in the catalytic core of the protein.

H129 is predicted to act in transition state stabilization by donating a proton to the leaving DNA 3'-OH during the cleavage of the sugar 3'-O-phosphate bond of DNA Mutations Generated for Dominant Negative Studies correspond to:

| P. furiosus | Human |
|---|---|
| H173 | H217 |
| H85 | H129 |

FIG. 5

Summary of Target Validation Studies: MRE11

Dominant negative studies

| | Antiproliferative Activity | | | | | | |
|---|---|---|---|---|---|---|---|
| | Tumor | | | | Normal | | |
| | A549 | Hela | PC3 | H1299 | HMEC | HUVEC | PrEC |
| Wt | | | | | | | |
| GFP-fusion | - | - | - | - | - | - | - |
| IRES GFP | - | - | nd | nd | - | - | nd |
| H217Y | | | | | | | |
| GFP-fusion | - | - | - | - | - | - | - |
| IRES GFP | - | - | nd | nd | - | - | nd |
| H129N | | | | | | | |
| GFP-fusion | ++ | ++ | -/+ | -/+ | - | - | - |
| IRES GFP | + | - | nd | nd | - | - | nd |

Antisense: A549 inconclusive ( + indicates antiproliferative effect in either the GFP positivity study, cell tracker or antisense studies)

FIG. 6

Summary of Target Validation Studies: MRE11

Dominant negative studies

|  | Chemosensitization Activity | | |
|---|---|---|---|
|  | Tumor A549 | Hela | HMEC |
| Wt GFP-fusion | - | - | - |
| H217Y GFP-fusion | ++ | ++ | - |

FIG. 7

Overexpression of MRE11 Wild Type and Mutants is Not Antiproliferative in Normal Cells Depletion of MRE11 is Antiproliferative in the Hyper-recombinogenic Chicken B-cell line DT40 Made Conditionally Null for MRE11

Additional phenotypes observed in MRE-/- cells

- chromosomal aberrations
- centrosome amplification
- enhanced sensitization to ionizing radiation EMBO J. 1999 Dec 1;18(23):6619-29.

Possible Models Explaining the Antiproliferative and Chemosensitization Effects of MRE11 Inhibition

Antiproliferative activity may be explained through MRE11's Role in:

- Double strand break repair
- Telomeric regulation

FIG. 24

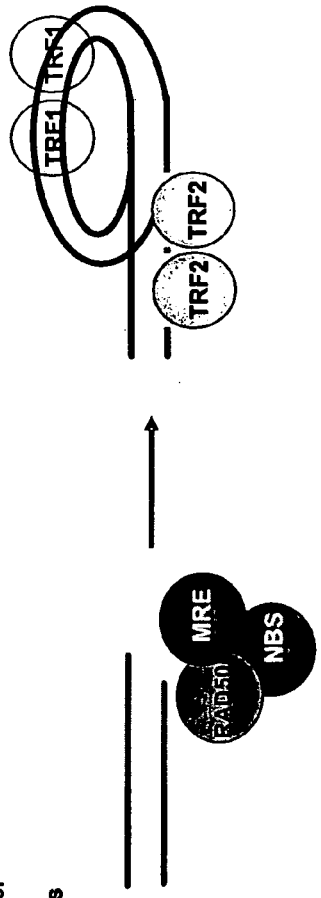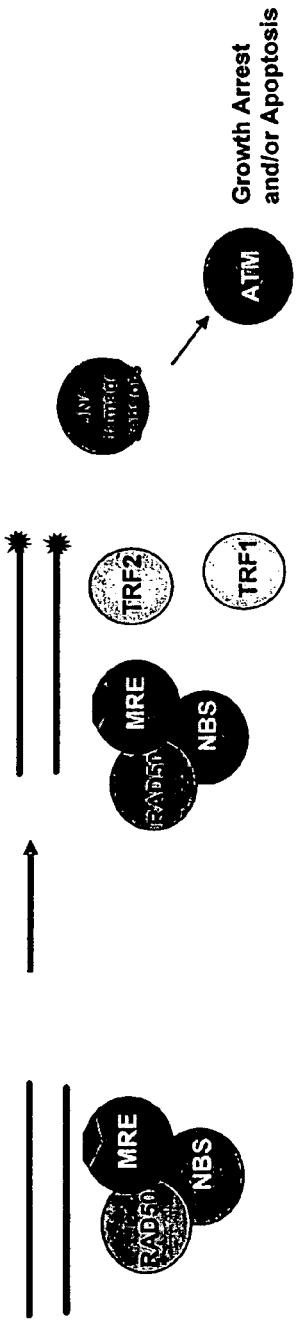
MRE11 Inhibition May Block the Formation of the Protective T-loop Structure at Telomere Ends
Wild Type MRE11
MRE11 may be required for proper preparation of telomeric DNA for strand invasion that protects telomeric ends
Mutant MRE11
FIG. 26

MRE11 Summary

Source: YTH- PCNA/Nbs1

Functional Studies

Antiproliferative Activity
- Overexpression of MRE11 H129N mutant protein is antiproliferative in tumor cells, but not in normal cells
- No strong antiproliferative effect is seen in cells expressing MRE11 wild type or H217Y mutant

Chemosensitization
- Overexpression of MRE11 H217Y mutant enhances sensitivity to chemotherapeutic treatment in tumor cells
- Sensitization by the H129N mutant cannot be assessed because of the inherent antiproliferative activity seen with expression of this mutant

Literature
- Numerous studies have suggested that MRE11 plays an important role in DNA damage repair pathway
- Studies on the yeast protein suggest that inhibition of catalytic activity of MRE11 will result in sensitivity to ionizing radiation

Conclusion
- Functional studies suggest inhibition of MRE11 will selectively inhibit tumor cell growth and enhance the response of tumor cells to DNA damaging agents

FIG. 27

Oligonucleotide Duplex Substrate for MRE11 Plate-Based Assay

Sequence was taken from oligonucleotide DG51 (Paul and Gellert, Mol. Cell, 1998), a substrate used to characterize the *in vitro* nuclease activity of recombinant Mre11. A *HaeIII* cleavage site was incorporated as a positive control for the assay.

PICOGREEN DYE ASSAY

FLUORESCENCE QUENCHING ASSAYS

US 7,358,040 B2

MRE 11: MODULATION OF CELLULAR PROLIFERATION

CROSS-REFERENCES TO RELATED APPLICATIONS

The present application claims priority to U.S. Ser. No. 60/309,737, filed Aug. 1, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of cellular proliferation. More particularly, the present invention is directed to nucleic acids encoding MRE11, which is a protein involved in modulation of cellular proliferation. The invention further relates to methods for identifying and using agents, including small molecule chemical compositions, antibodies, peptides, cyclic peptides, nucleic acids, antisense nucleic acids, RNAi, and ribozymes, that modulate cellular proliferation via modulation of MRE11; as well as to the use of expression profiles and compositions in diagnosis and therapy related to modulation of cellular proliferation, e.g., in diseases such as cancer.

BACKGROUND OF THE INVENTION

Double and single-stranded breaks occur in chromosomal DNA during normal cell cycle progression, or after exposure to ionizing regulation or other mutagens, or during homologous recombination. Eukaryotic cells have multiple pathways for repairing DNA breaks, as chromosomal breaks can be lethal to the cell if they are not repaired. Ends can be repaired by homologous recombination, or by joining of non-homologous ends (see, e.g., Roth et al., Mol. Cell. Biol. 5:2599-2607 (1985); Roth & Wilson, Proc. Nat'l Acad. Sci. USA 82:3355-3359 (1985)). Enzymes involved in such pathways have been implicated in diseases related to cellular proliferation, such as cancer. Thus, there is a need to establish screening assays for understanding human diseases caused by disruption of DNA repair pathways. Identifying proteins, their ligands and substrates, and downstream signal transduction pathways involved in neoplasia in humans is important for developing therapeutic regents to treat cancer and other proliferative diseases.

BRIEF SUMMARY OF THE INVENTION

The present invention therefore provides nucleic acids encoding meiotic recombination 11 (MRE11), which is a nuclease protein with exo- and endonuclease activity involved in modulation of DNA damage assessment and checkpoint regulation, and cellular proliferation. The present invention shows for the first time that mutant MRE11 is antiproliferative in tumor cells. The invention therefore provides methods of screening for compounds, e.g., small organic molecules, antibodies, peptides, cyclic peptides, nucleic acids, antisense molecules, RNAi, and ribozyme, that are capable of modulating cellular proliferation, e.g., either inhibiting cellular proliferation or activating apoptosis. The compounds of the invention are also useful for enhancing sensitivity of a cell to chemotherapeutic agents such as bleomycin and etoposide, and/or reducing toxicity of chemotherapeutic agents. Therapeutic and diagnostic methods and reagents are also provided. Modulators of MRE11 are therefore useful in treatment of cancer, inflammation, and other diseases involving cellular proliferation.

In one aspect, the present invention provides a method for identifying a compound capable of interfering with binding of an MRE11 polypeptide or fragment thereof, the method comprising the steps of: (i) combining an MRE11 polypeptide or fragment thereof with a polypeptide selected from the group consisting of RAD50 and NSB1, and the compound, wherein the MRE11 polypeptide or fragment thereof has nuclease activity and is encoded by a nucleic acid that hybridizes under stringent conditions to a nucleic acid encoding a polypeptide having an amino acid sequence of SEQ ID NO:2; and (ii) determining the binding of the MRE11 polypeptide or fragment thereof to a polypeptide selected from the group consisting of RAD50 and NSB1.

In one embodiment, the MRE11 polypeptide or fragment thereof and the RAD50 or NSB1 polypeptide are combined first. In another embodiment, the MRE11 polypeptide or fragment thereof and the RAD50 and NSB1 polypeptide are combined. In another embodiment, the MRE11 polypeptide or fragment thereof and the RAD50 or NSB1 polypeptide are expressed in a cell, e.g., a mammalian cell or a yeast cell. In another embodiment, the MRE11 polypeptide or fragment thereof is fused to a heterologous polypeptide. In another embodiment, the binding of the MRE11 polypeptide or fragment thereof to RAD50 or NSB1 is determined by measuring reporter gene expression.

In another aspect, the present invention provides a method for identifying a compound that modulates cellular proliferation or chemosensitivity, the method comprising the steps of: (i) contacting the compound with an MRE11 polypeptide, the polypeptide encoded by a nucleic acid that hybridizes under stringent conditions to a nucleic acid encoding a polypeptide having an amino acid sequence of SEQ ID NO:2; and (ii) determining the functional effect of the compound upon the MRE11 polypeptide.

In one embodiment, the functional effect is measured in vitro. In another embodiment, the polypeptide is expressed in a eukaryotic host. In another embodiment, the functional effect is a physical effect, e.g., ligand or substrate binding. In another embodiment, the functional effect is a chemical effect, e.g., enzymatic activity such as endo- or exo-nuclease activity. In another embodiment, the chemical or phenotypic effect is determined by measuring cellular proliferation, e.g., by measuring DNA synthesis or fluorescent marker dilution. In another embodiment, DNA synthesis is measured by $^3$H thymidine incorporation, BrdU incorporation, or Hoescht staining. In another embodiment, the fluorescent marker is selected from the group consisting of a cell tracker dye or green fluorescent protein.

In another embodiment, modulation is inhibition of cellular proliferation, e.g., cancer cell proliferation. In another embodiment, modulation is activating sensitivity to chemotherapeutic reagents, e.g., cancer cell sensitivity to chemotherapeutic reagents. In another embodiment, the host cell is a cancer cell, e.g., a breast, prostate, colon, or lung cancer cell. In another embodiment, the cancer cell is a transformed cell line, e.g., PC3, H1299, MDA-MB-231, MCF7, A549, or HeLa. In another embodiment, the cancer cell is p53 null, p53 mutant, or p53 wild-type. In another embodiment, the cancer cell is treated with bleomycin or etoposide.

In another embodiment, the polypeptide is recombinant. In another embodiment, the polypeptide is encoded by a nucleic acid having a sequence of SEQ ID NO:1. In another embodiment, the compound is an antibody, antisense oligonucleotide, small organic compound, peptide, or circular peptide.

In another aspect, the present invention provides a method for identifying a compound that modulates cellular proliferation or chemosensitivity, the method comprising the steps of: (i) contacting the compound with an MRE11 polypeptide or a fragment thereof, the MRE11 polypeptide or fragment thereof encoded by a nucleic acid that hybridizes under stringent conditions to a nucleic acid encoded by a polypeptide comprising an amino acid sequence of SEQ ID NO:2; (ii) determining the physical effect of the compound upon the MRE11 polypeptide; and (iii) determining the chemical or phenotypic effect of the compound upon a cell comprising an MRE11 polypeptide or fragment thereof, thereby identifying a compound that modulates cellular proliferation or chemosensitivity.

In another aspect, the present invention provides a method of modulating cellular proliferation in a subject, the method comprising the step of administering to the subject a therapeutically effective amount of a compound identified using the methods described above.

In one embodiment, the subject is a human. In another embodiment, the subject has cancer.

In another aspect, the present invention provides a method of modulating cellular proliferation in a subject, the method comprising the step of administering to the subject a therapeutically effective amount of a MRE11 polypeptide, the polypeptide encoded by a nucleic acid that hybridizes under stringent conditions to a nucleic acid encoding a polypeptide having an amino acid sequence of SEQ ID NO:2.

In another aspect, the present invention provides a method of modulating cellular proliferation in a subject, the method comprising the step of administering to the subject a therapeutically effective amount of a nucleic acid encoding a MRE11 polypeptide, wherein the nucleic acid hybridizes under stringent conditions to a nucleic acid encoding a polypeptide having an amino acid sequence of SEQ ID NO:2.

BRIEF DESCRIPTION OF THE DRAWINGS

FIG. 1 shows a human nucleotide sequence (SEQ ID NO:1) of MRE11.

FIG. 2 shows a human amino acid sequence (SEQ ID NO:2) of MRE11.

FIG. 4 shows dominant negative mutants generated for target validation studies. hMRE11=SEQ ID NO:3; SCNMRE11=SEQ ID NO:4; consensus peptides=SEQ ID NOS:5-18.

FIG. 5 shows a representation of the active site of *P. furiosus* MRE11.

FIGS. 6-7 shows a summary of target validation studies for MRE11.

FIG. 24 shows possible models explaining the antiproliferative and chemosensitization effects of MRE11 inhibition.

FIG. 26 shows that MRE11 inhibition may block the formation of the protective T-loop structure at telomere ends.

FIG. 27 provides a summary of MRE11 activity.

DETAILED DESCRIPTION OF THE INVENTION

Introduction

Figure 3:
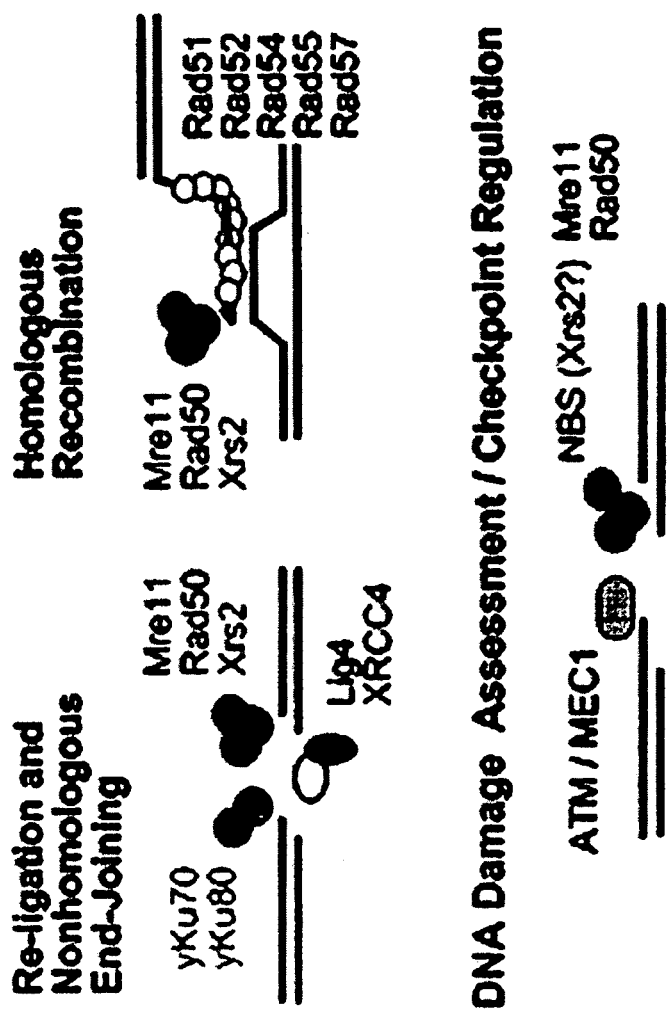
FIG. 3 shows a schematic representation of MRE11 activity.
Figure 8:
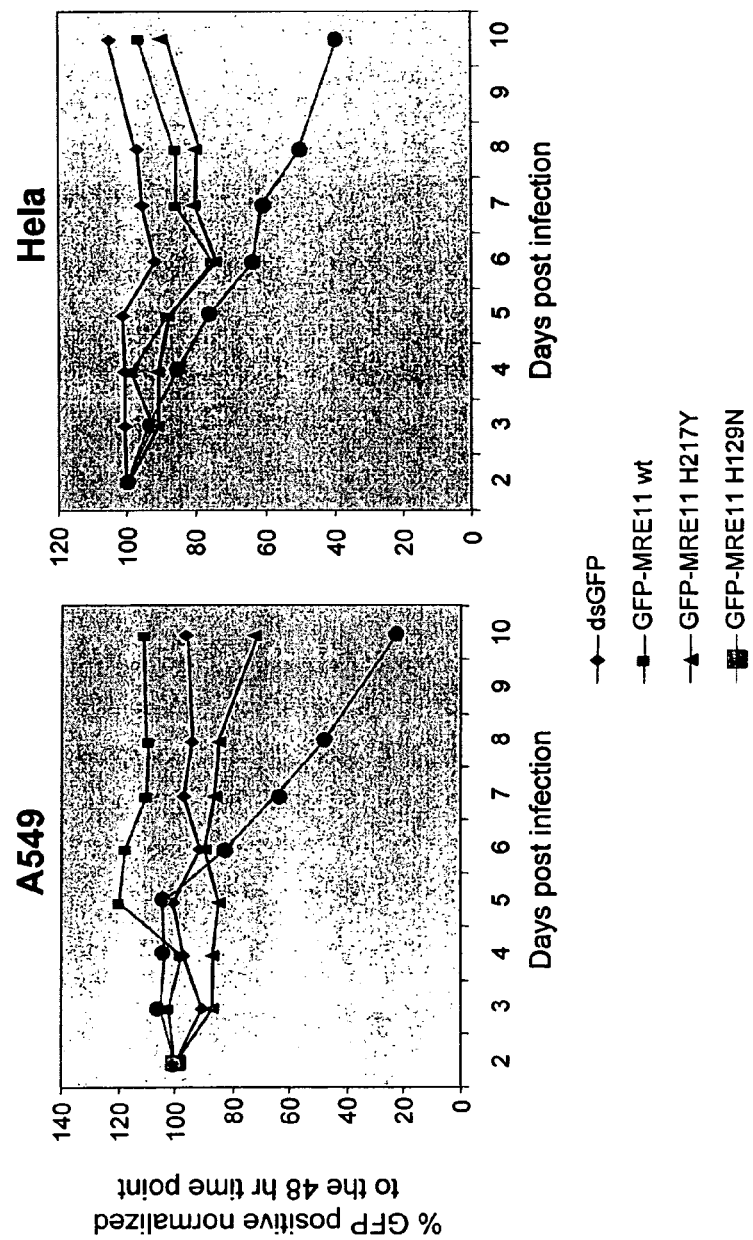
FIG. 8 shows data demonstrating that overexpression of GFP-fused MRE11 H129N mutant is antiproliferative in A549 tumor cells and HeLa cells.
Figure 9:
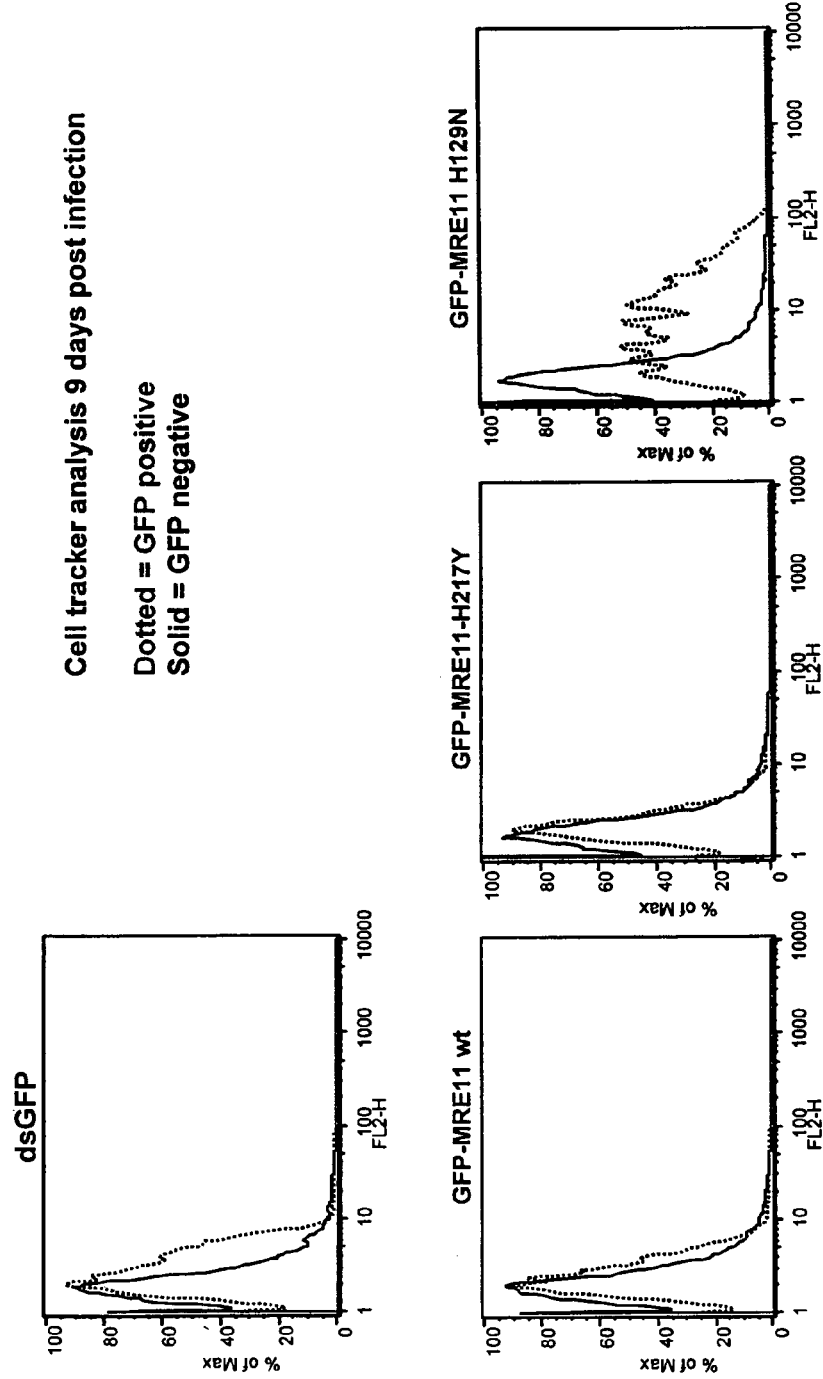
FIG. 9 shows cell tracker assay data demonstrating that the activity of GFP-fused MRE11 H129N mutant is antiproliferative in A549 tumor cells.
Figure 10:
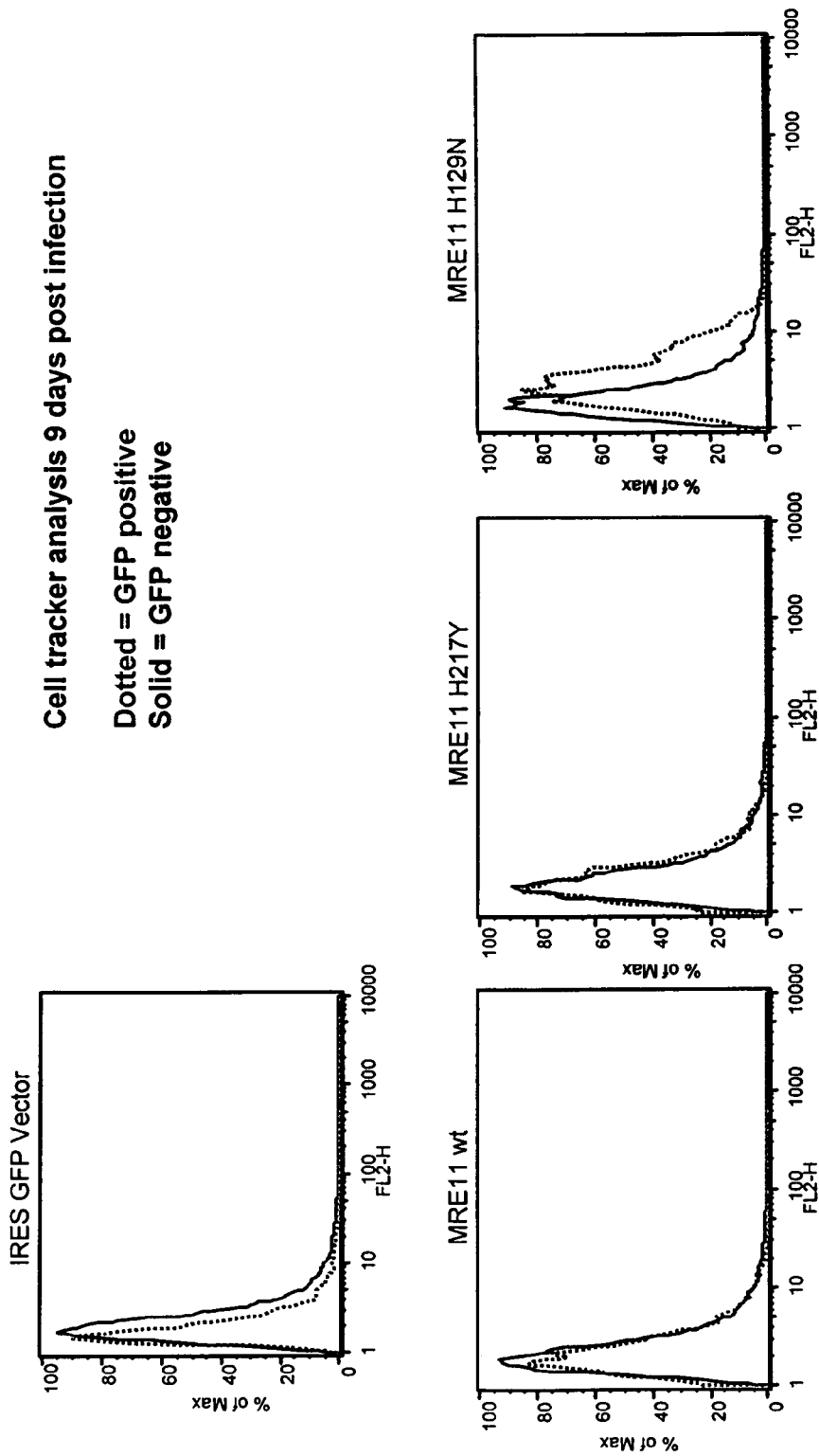
FIG. 10 shows cell tracker assay data demonstrating that the activity of MRE11 H129N mutant using IRES GFP is antiproliferative in A549 tumor cells.
Figure 11:
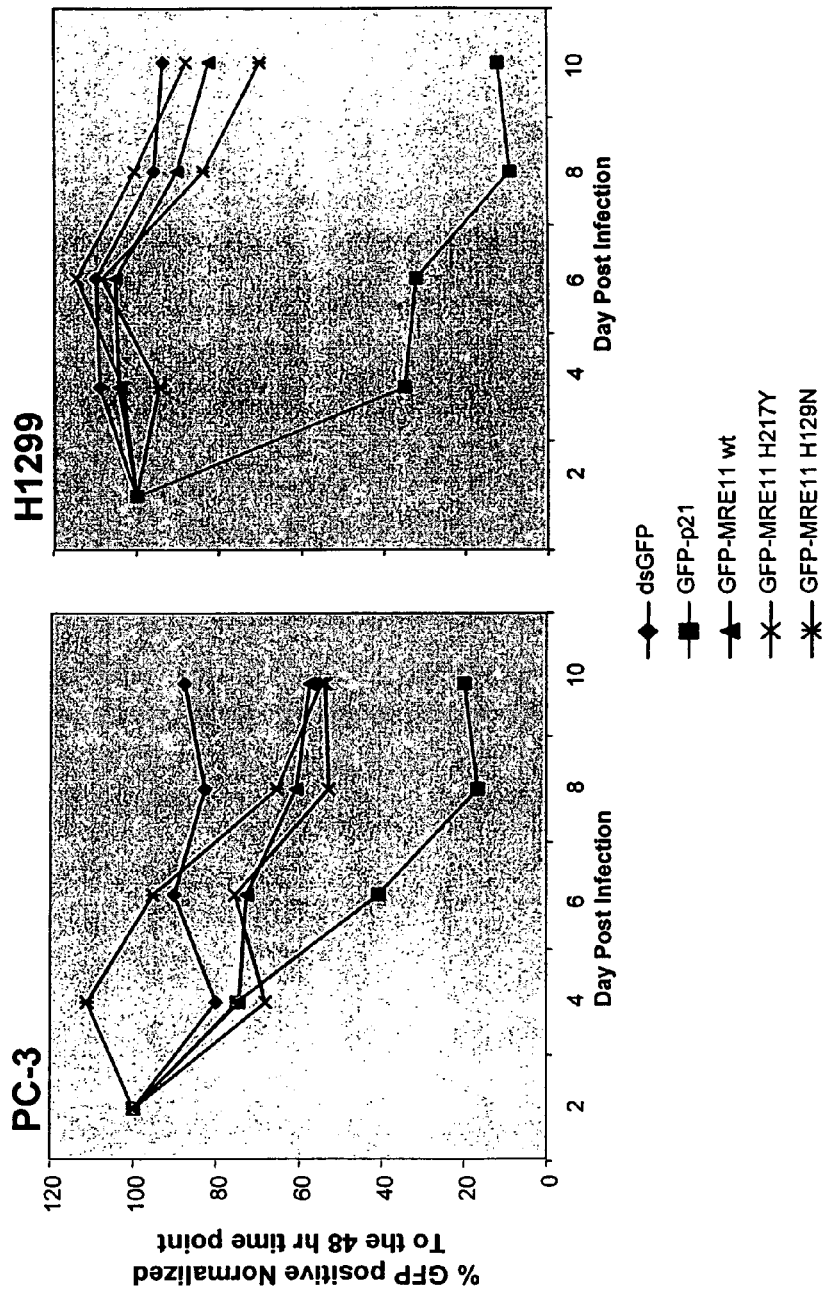
FIG. 11 shows overexpression of GFP-fused MRE11 wild-type and mutants in PC-3 and H1299 cells.
Figure 12:
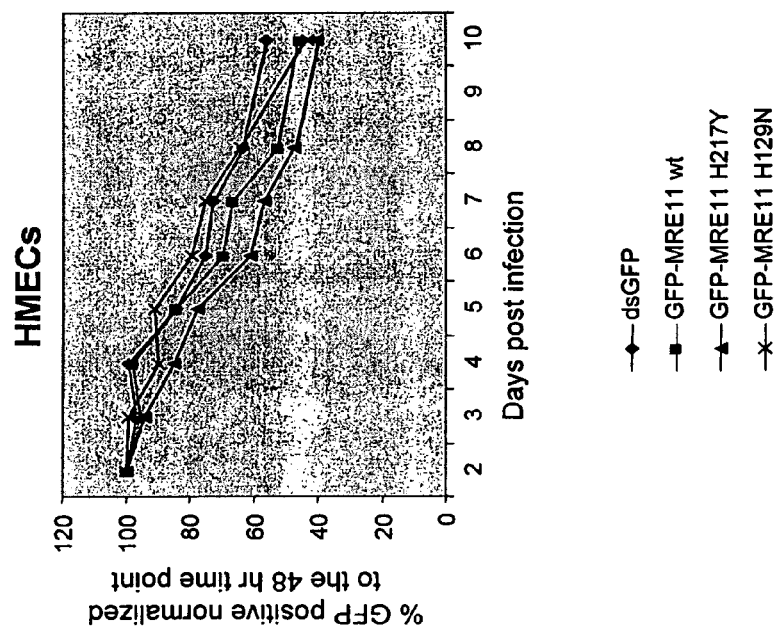
FIG. 12 shows data demonstrating that MRE11 wild type and mutant is not antiproliferative in normal cells.
Figure 13:
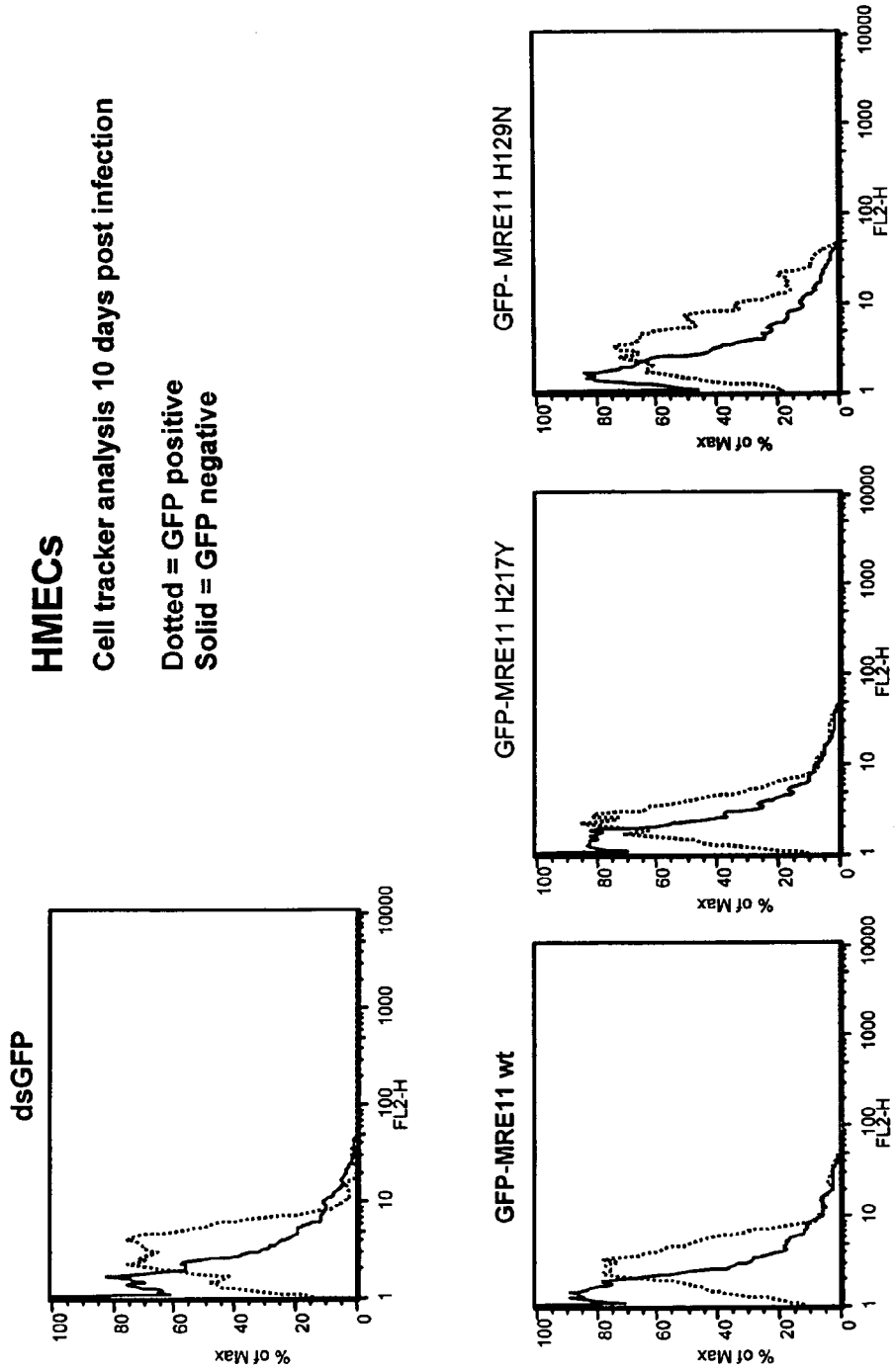
FIG. 13 shows data demonstrating that no antiproliferative activity of MRE11 wild-type or mutant proteins is detected by the cell tracker assay in normal cells.
Figure 14:
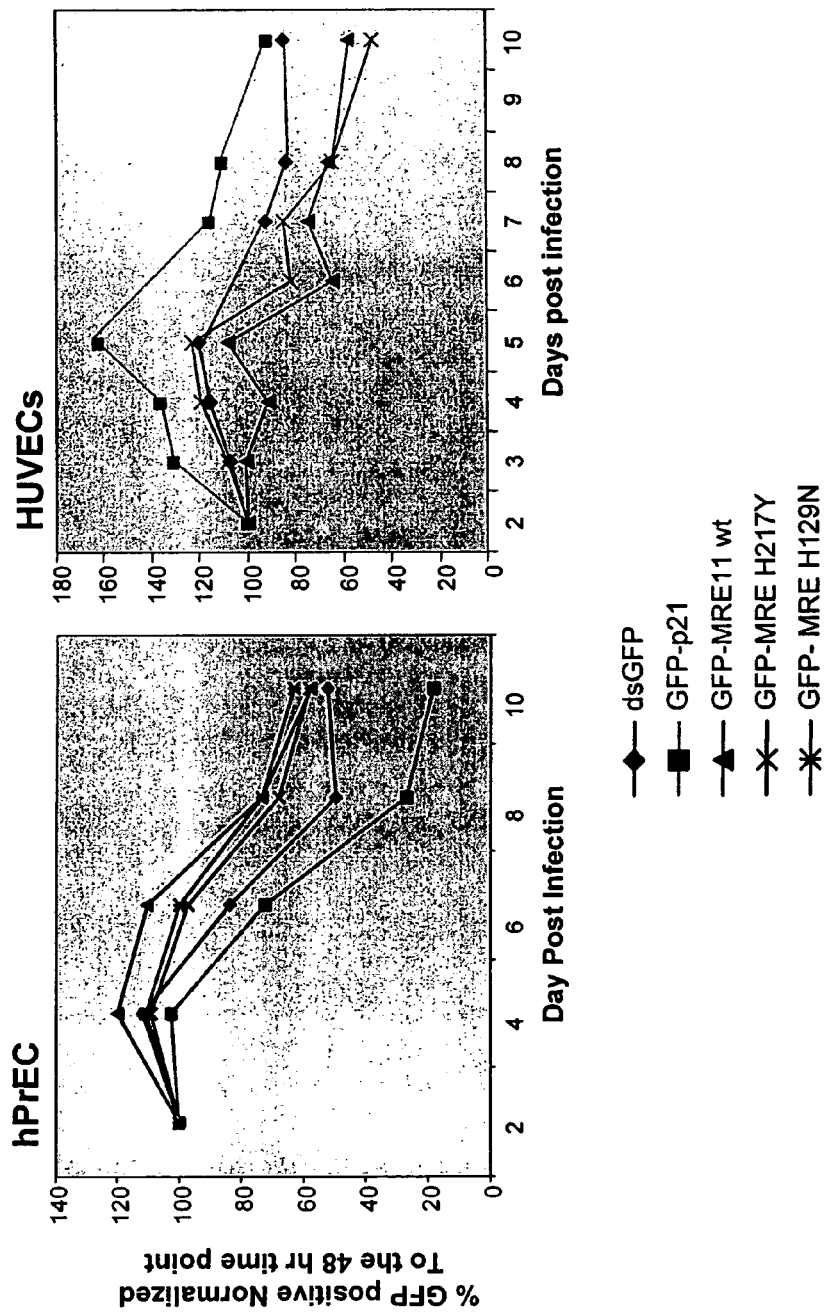
FIG. 14 shows overexpression of MRE11 wild-type and mutants is not antiproliferative in normal cells.
Figure 15:
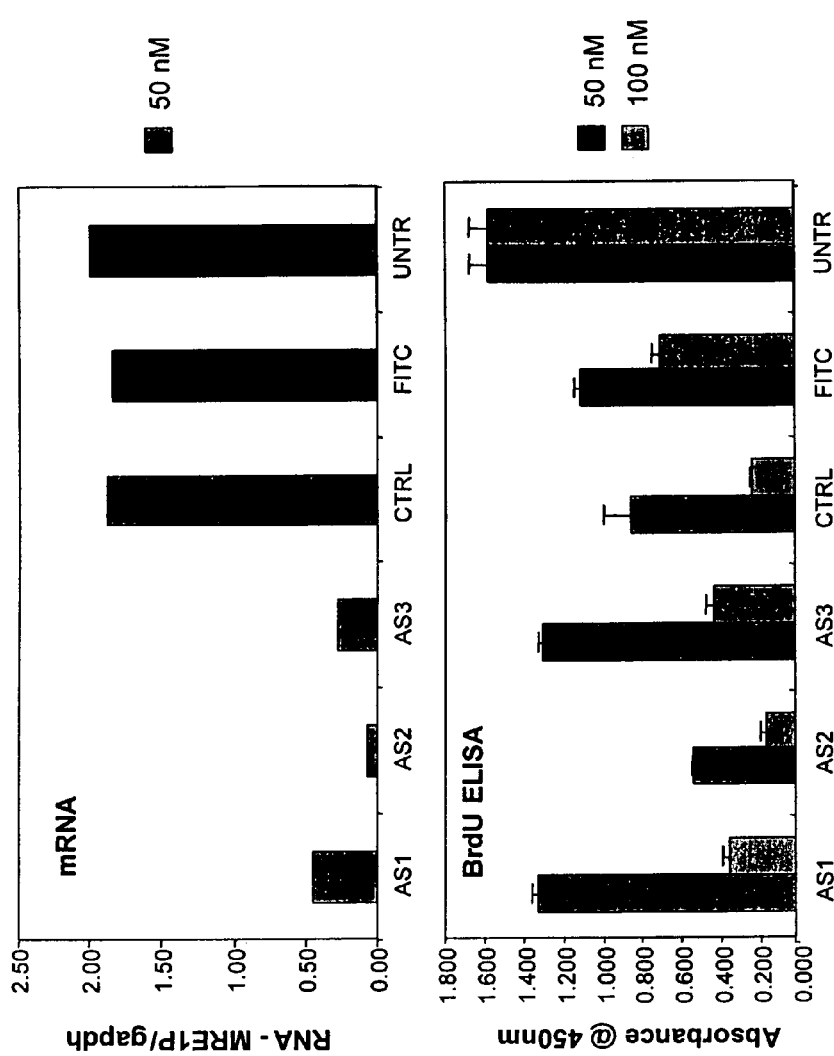
FIG. 15 shows MRE11 specific antisense oligo effects in A549 cells.
Figure 16:
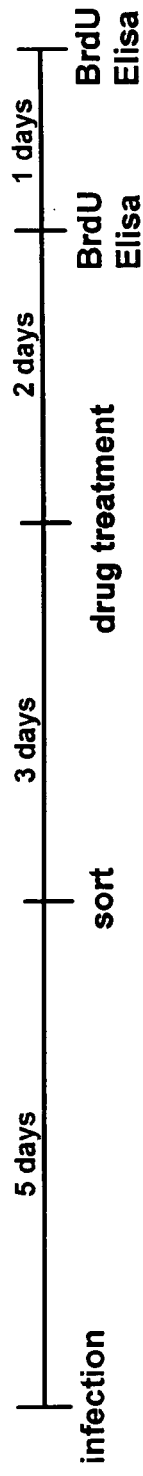
FIG. 16 shows strategies for assessing chemosensitization using dominant negative studies.
Figure 17:
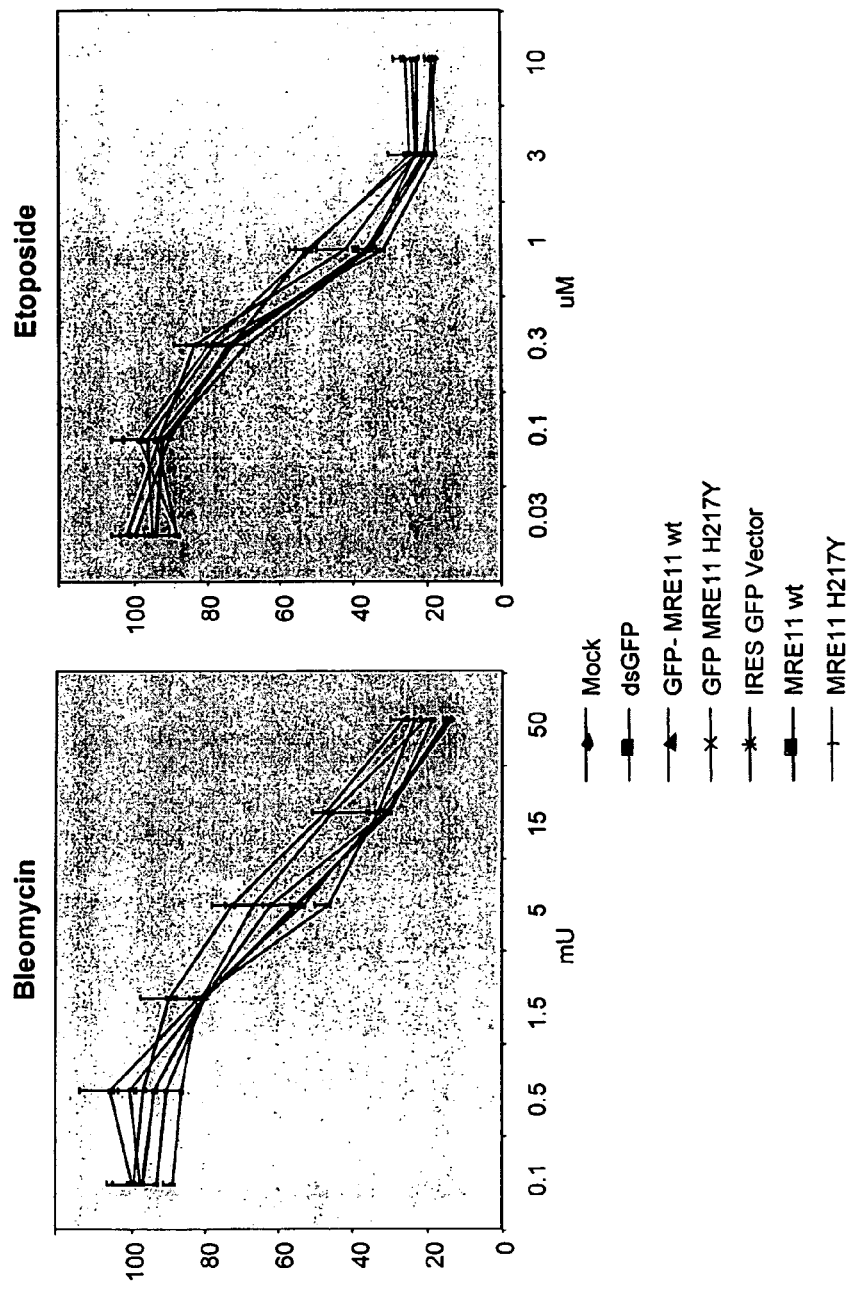
FIG. 17 shows plate based chemosensitization studies of sorted HeLa cells expression GFP-fused wild-type or mutant MRE11.
Figure 18:
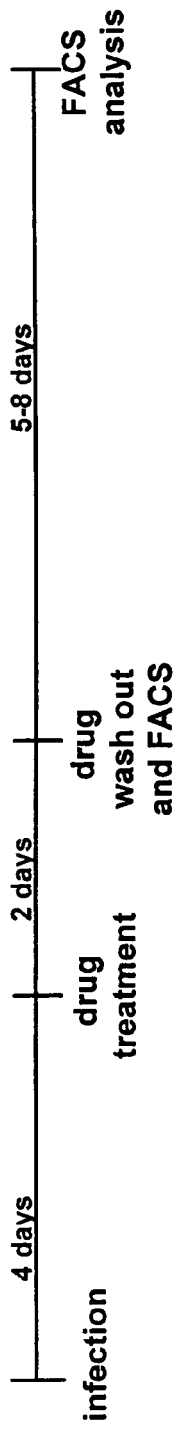
FIG. 18 shows additional strategies for assessing dominant negative chemosensitization effects.
Figure 19A:
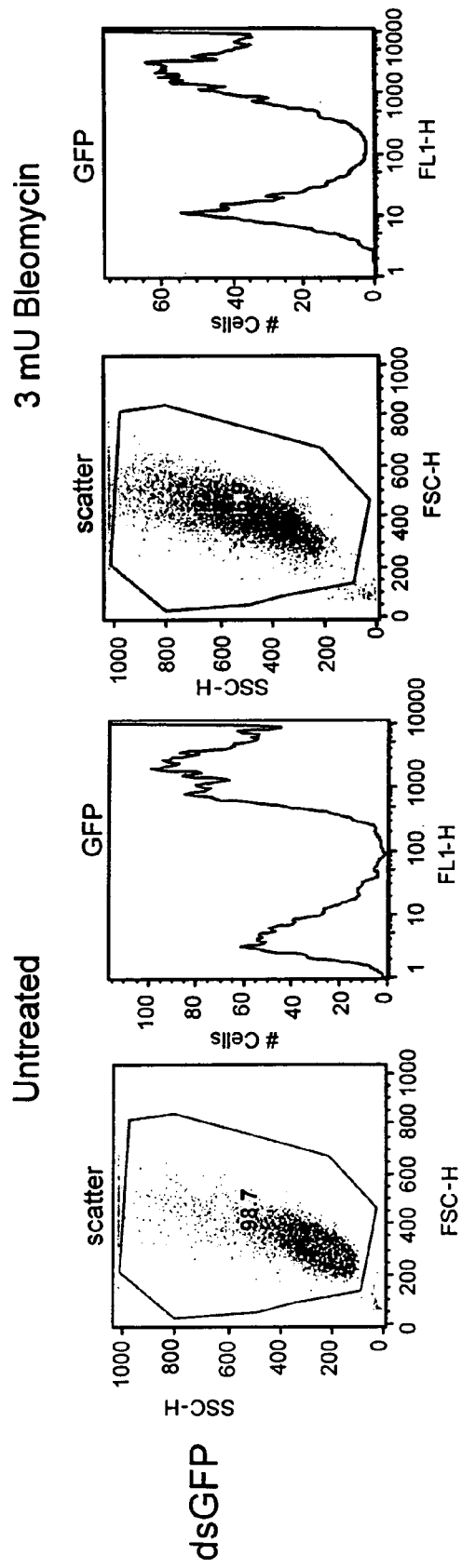
FIG. 19 shows no selective sensitization of MRE11 wild type or mutant expression A540 tumor cells 48 hours after bleomycin treatment.
Figure 19B:
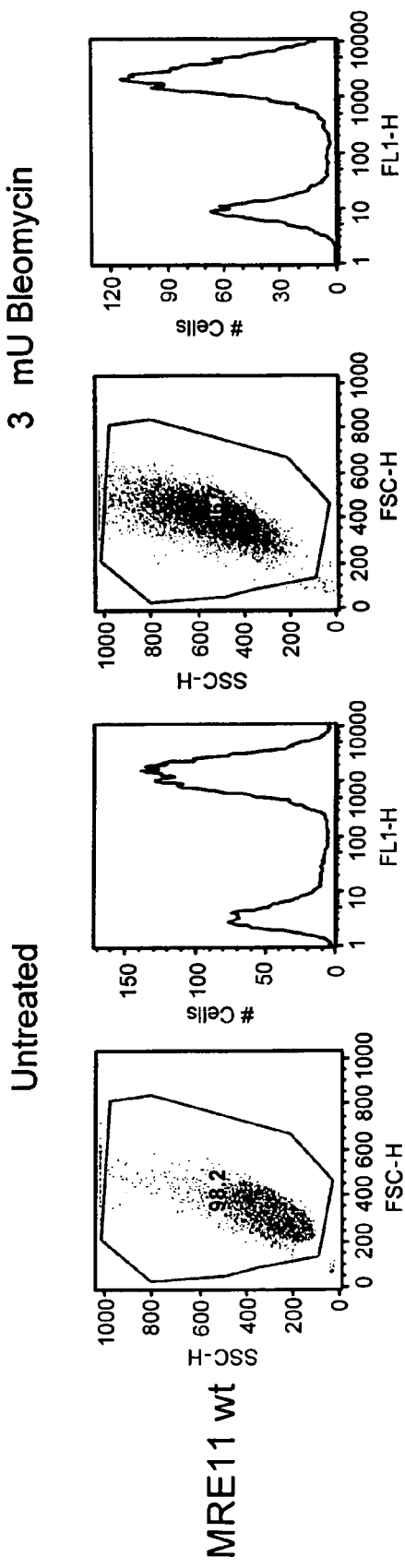
Figure 19C:
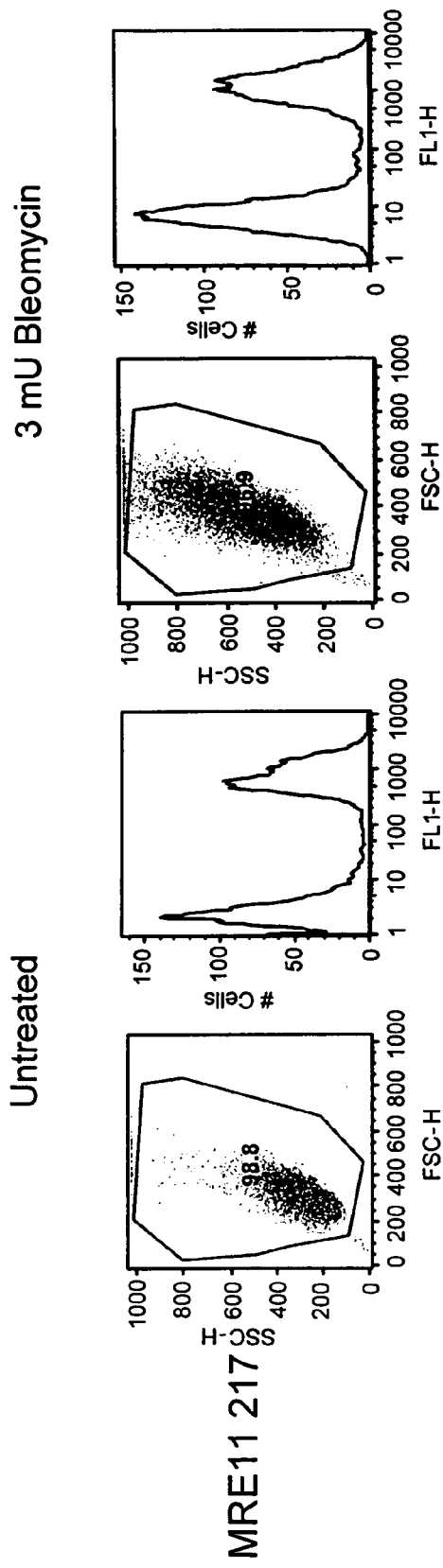
Figure 20A:
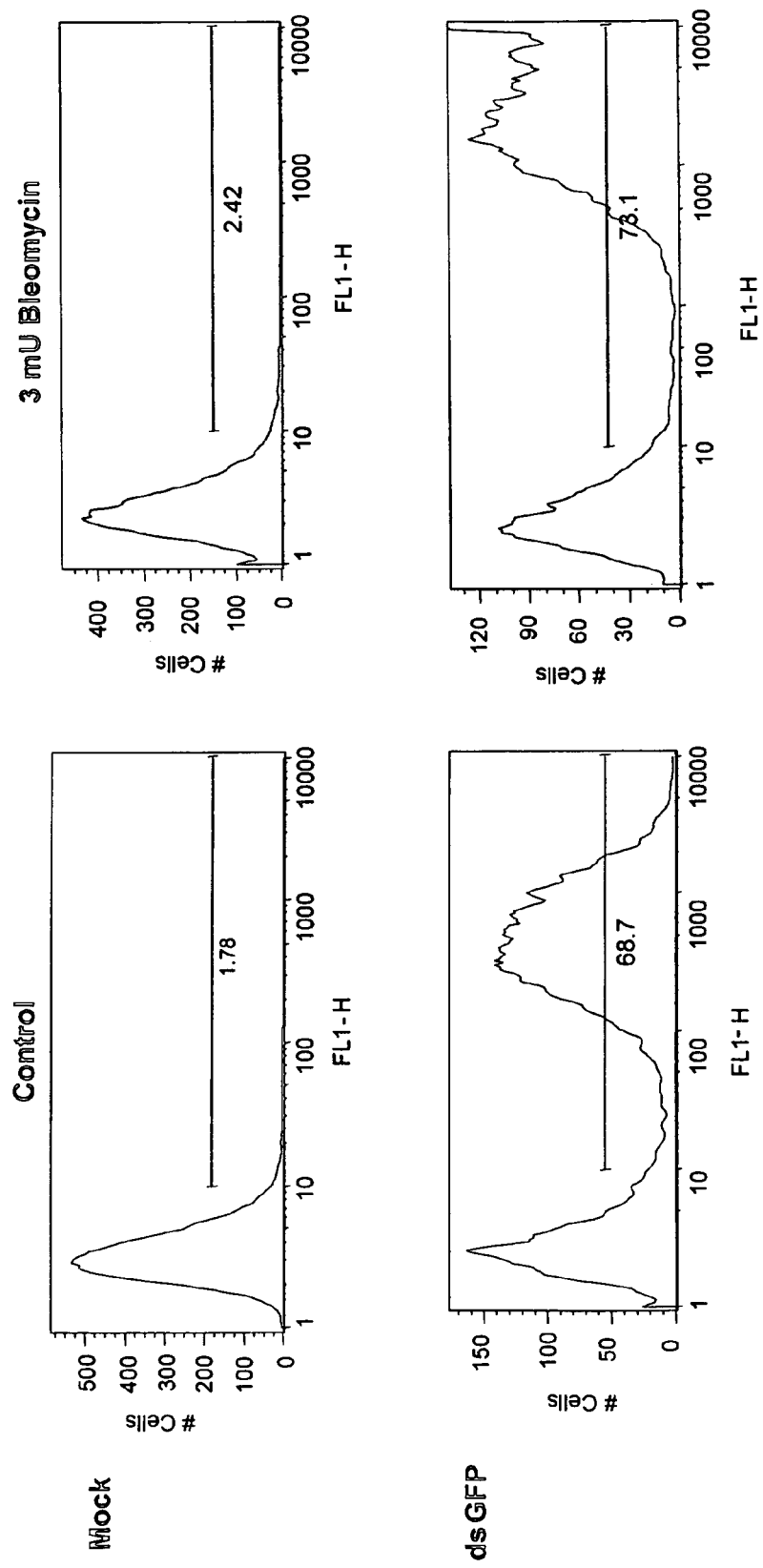
FIG. 20 shows that A549 cells expressing MRE11 H217Y mutant fail to recover from bleomycin treatment.
Figure 20B:
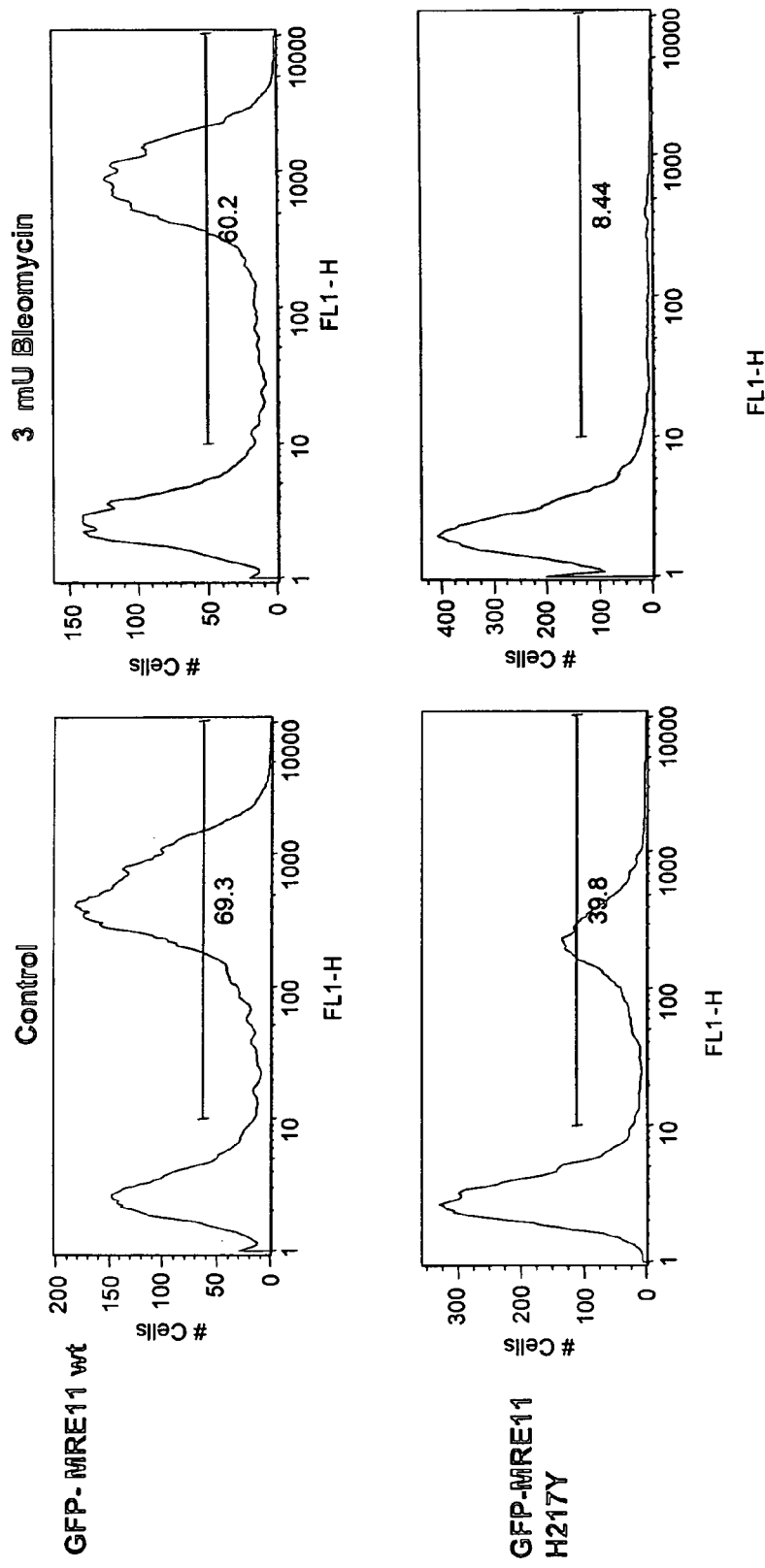
Figure 21:
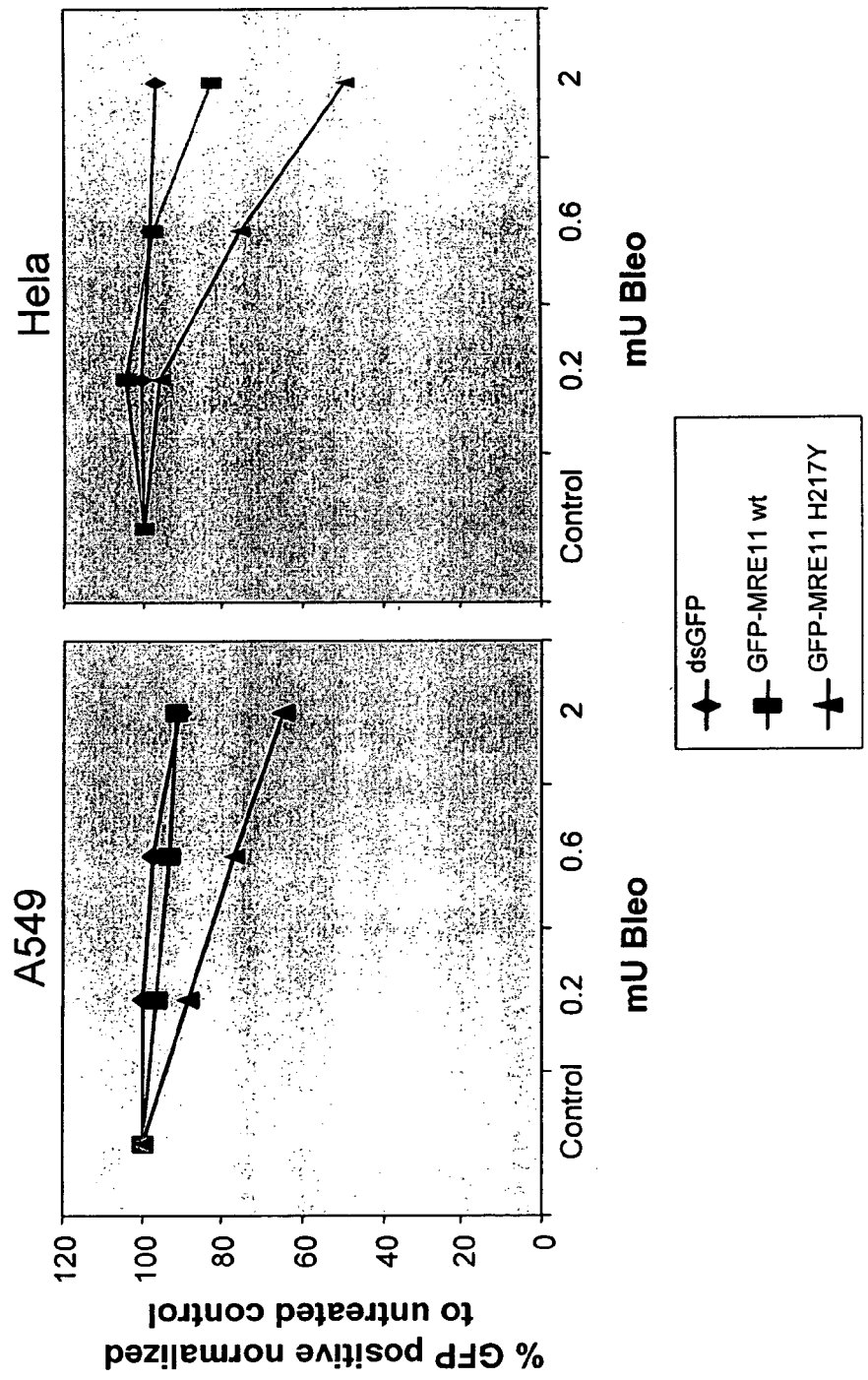
FIG. 21 shows that overexpression of GFP-MRE11 H217Y mutant in A549 tumor cells and HeLa cells enhances sensitivity to bleomycin treatment.
Figure 22:
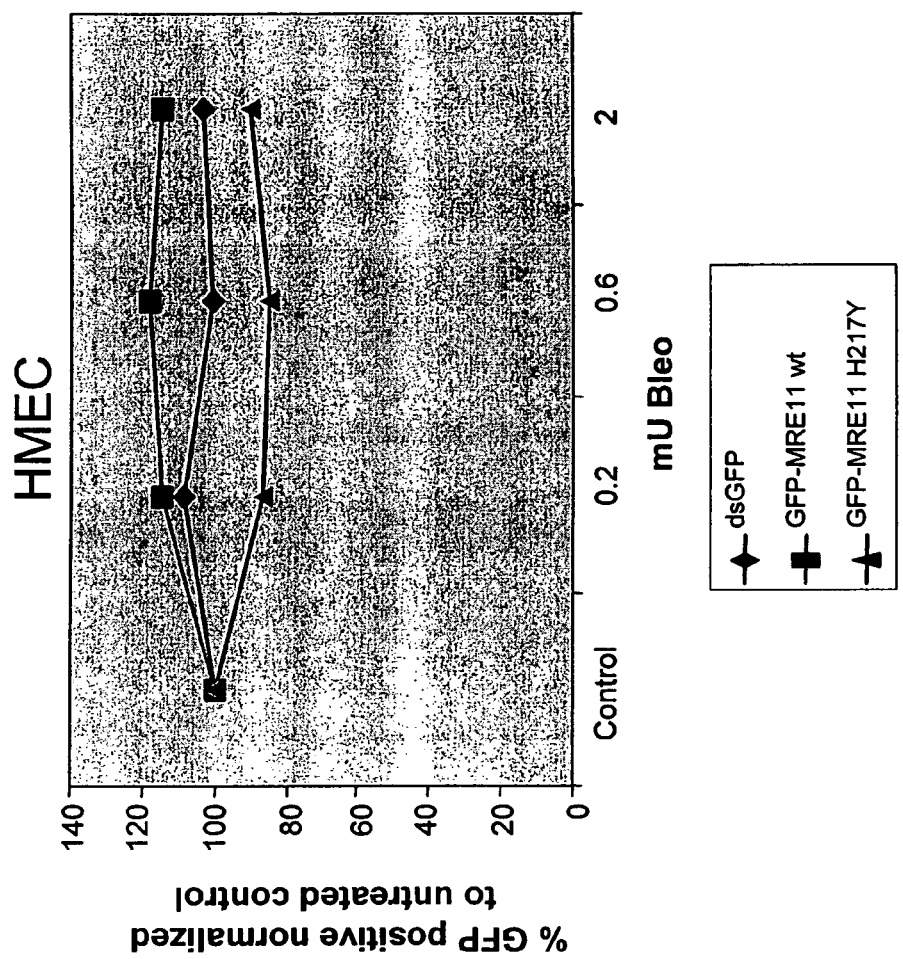
FIG. 22 shows that overexpression of GFP-MRE11 H217Y mutant in normal HMEC cells does not enhance sensitivity to bleomycin treatment.
Figure 23:
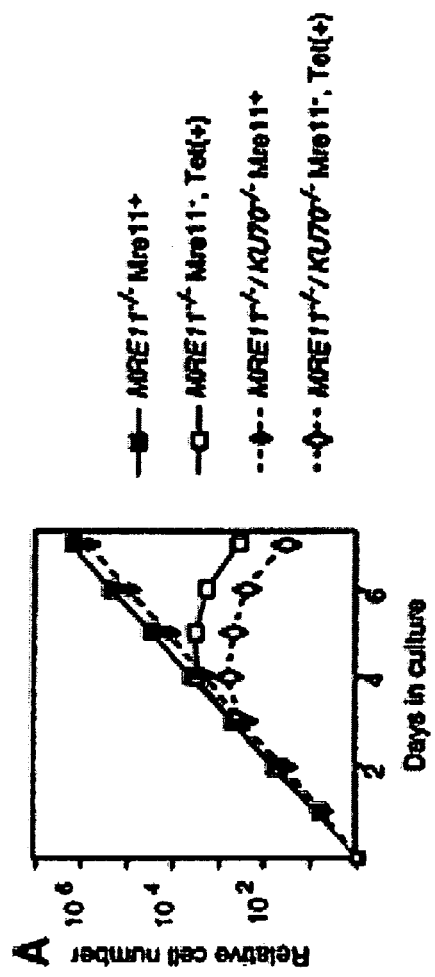
FIG. 23 shows that depletion of MRE11 is antiproliferative in the hyper-recombinogenic chicken B-cell line DT40 made conditionally null for MRE11.
Figure 25:
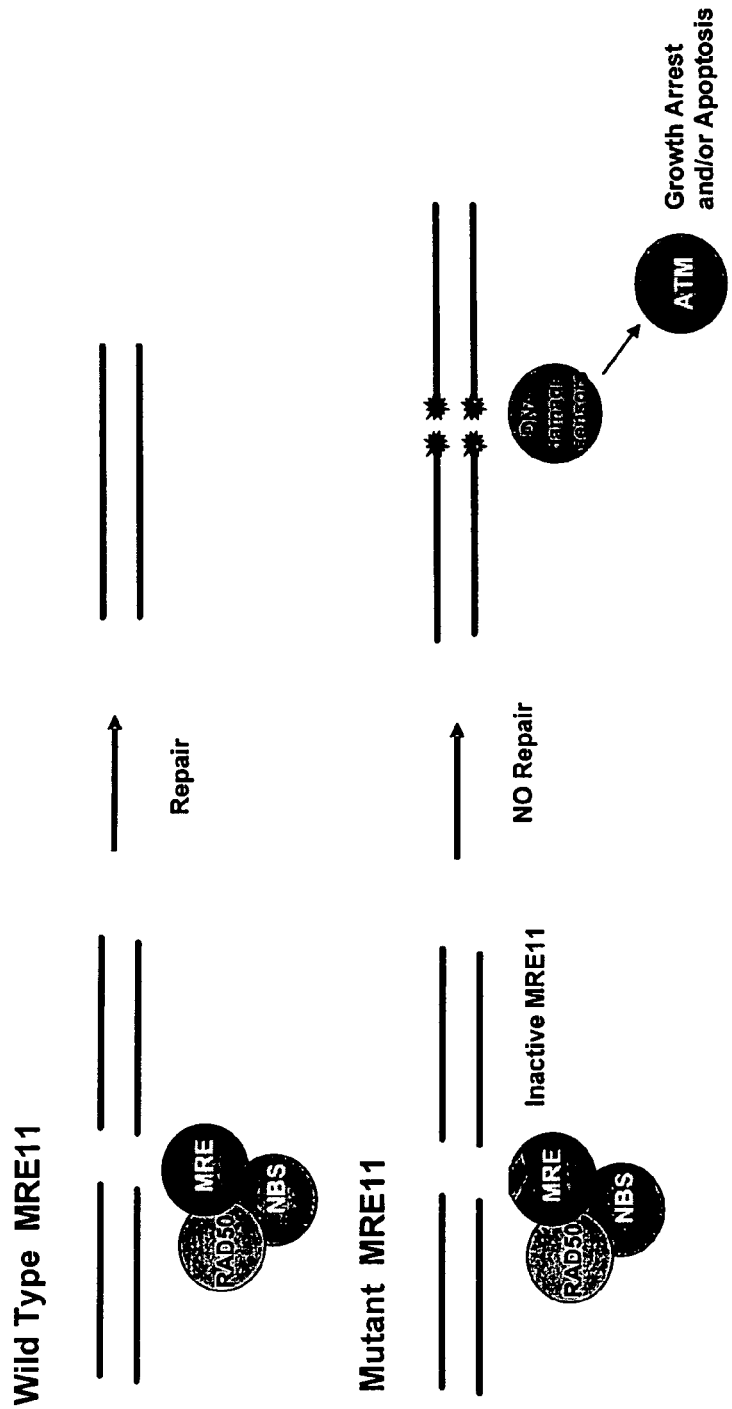
FIG. 25 shows that MRE11 may block repair of spontaneous or drug-induced double strand breaks.

In mammalian cells, MRE11, RAD50, and NBS1 protein associate with one another in a multiprotein complex involved in the cellular DNA repair response (see, e.g., Petrini, *Am. J Hum. Genet.* 64:1264-1269 (1999)). MRE11 has endo and exonuclease activity, and its crystal structure has been reported using *Pyrococcus furiosus* MRE11 (see, e.g., Paull & Gellert, *Mol. Cell,* 1:969-979 (1998); and Hopfner et al., *Cell* 105:473-485 (2001)). Recent studies have shown that MRE11 is mutated in individuals with ataxiatelangiectasia-like disorder (see, e.g., Stewart et al., *Cell* 99:577-587 (1999). In addition, in Nijmegen breakage syndrome, a disease characterized by immunodeficiency, genomic instability, and cancer susceptibility, the defective gene product p95 associates with MRE11 and RAD50 (see, e.g., Lombard & Guarente, *Cancer Res.* 60:2331-2334 (2000)). Finally, studies have found occasional MRE11 mutations in some primary tumors (see, e.g., Fukuda et al., *Cancer Res.* 61:23-26 (2001)). However, MRE11 involvement in transformation and tumorigenesis has never been demonstrated. The present invention demonstrates for the first time that inhibition of MRE11 is antiproliferative in tumor cells, and demonstrates a role for MRE11 in cellular proliferation, transformation, and enhancement of sensitivity to chemotherapeutic reagents.

As described below, the present inventors identified MRE11 in a yeast two hybrid assay, using PCNA as bait. Another molecule, NBS1, was identified in the two-hybrid assay as a PCNA-binding protein, as NBS1 binds the mammalian homolog of yeast RAD50, which also binds to MRE11 (see, e.g., Petrini, *Am. J Hum. Genet.* 64:1264-1269 (1999); Kim et al., *J. Biol. Chem.* 271:29255-29264 (1996); see also GenBank Accession number XP_034864 for a protein sequence of human RAD50 and Accession number XM_034864 for a nucleic acid sequence of human RAD50; see also Example 1)). NBS1 therefore bound to the RAD50/MRE11 complex, as well as to PCNA. As shown in FIGS. 8-15, inhibition of MRE11 or overexpression of an MRE11 mutant is antiproliferative in tumor cells and HeLa cells but not in normal cells (using, e.g., GFP positivity assays, cell tracker assays, and antisense assays). FIGS. 16-22 demonstrate that overexpression of an MRE11 mutant enhances sensitivity to chemotherapeutic reagents in tumor cells. These functional studies, presented herein, demonstrate, e.g., that inhibition of MRE11 will inhibit tumor cell growth and enhance chemosensitivity to compounds such as bleomycin and etoposide.

MRE11 therefore represents a drug target for compounds that suppress or activate cellular proliferation, or cause cell cycle arrest, cause release from cell cycle arrest, increase sensitivity to chemotherapeutic reagents such as bleomycin and etoposide, and decrease toxicity of chemotherapeutic reagents. Agents identified in these assays, including small organic molecules, antibodies, peptides, cyclic peptides, nucleic acids, antisense nucleic acids, RNAi, and ribozymes, that modulate cellular proliferation via modulation of MRE11, can be used to treat diseases related to cellular proliferation, such as cancer and inflammation. In particular, inhibitors of MRE11 are useful for inhibition of cancer and tumor cell growth. MRE11 activators can also be used to induce apoptosis. MRE11 modulators can also be used to modulate the sensitivity of cells to chemotherapeutic agents, such as bleomycin and etoposide, and other agents known to those of skill in the art. MRE11 modulators can also be used to decrease toxicity of such chemotherapeutic reagents.

Such modulators are useful for treating cancers, such as melanoma, breast, ovarian, lung, gastrointestinal and colon, prostate, and leukemia and lymphomas, e.g., multiple myeloma. In addition, such modulators are useful for treating noncancerous disease states caused by pathologically proliferating cells such as thyroid hyperplasia (Grave's disease), inflammation, psoriasis, benign prostatic hypertrophy, neurofibromas, atherosclerosis, restenosis, and other vasoproliferative disease.

Definitions

By "disorder associated with cellular proliferation" or "disease associated with cellular proliferation" herein is meant a disease state which is marked by either an excess or a deficit of cellular proliferation. Such disorders associated with increased cellular proliferation include, but are not limited to, cancer and non-cancerous pathological proliferation.

The terms "MRE11" or a nucleic acid encoding "MRE11" refer to nucleic acids and polypeptide polymorphic variants, alleles, mutants, and interspecies homologs that:

(1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by an MRE11 nucleic acid (for a human MRE11 nucleic acid sequence, see, e.g., FIG. 1, SEQ ID NO:1, or Accession number NM_005591) or amino acid sequence of an MRE11 protein (for a human MRE11 protein sequence, see, e.g., FIG. 2, SEQ ID NO:2 or Accession number NP_005582); (2) bind to antibodies, e.g., polyclonal antibodies, raised against an immunogen comprising an amino acid sequence of an MRE11 protein, and conservatively modified variants thereof; (3) specifically hybridize under stringent hybridization conditions to an anti-sense strand corresponding to a nucleic acid sequence encoding an MRE11 protein, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to an MRE11 nucleic acid. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. A MRE11 protein typically has nuclease activity, e.g., endonuclease and/or exonuclease activity.

The phrase "functional effects" in the context of assays for testing compounds that modulate activity of an MRE11 protein includes the determination of a parameter that is indirectly or directly under the influence of an MRE11, e.g., an indirect, phenotypic or chemical effect, such as the ability to increase or decrease cellular proliferation, apoptosis, DNA repair, homologous recombination, cell cycle arrest, or nuclease activity; or e.g., a direct, physical effect such as ligand or substrate binding or inhibition of ligand or substrate binding. A functional effect therefore includes ligand binding activity, substrate binding activity, the ability of cells to proliferate, apoptosis, and enzyme activity, such as endo- and exo-nuclease activity. "Functional effects" include in vitro, in vivo, and ex vivo activities. FIGS. 28 and 30-33 shows examples of biochemical high throughput assays that measure enzymatic activity.

By "determining the functional effect" is meant assaying for a compound that increases or decreases a parameter that is indirectly or directly under the influence of an MRE11 protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand or substrate binding activity; measuring cellular proliferation; measuring apoptosis; measuring cell surface marker expression; measurement of changes in protein levels for MRE11 associated sequences; measurement of RNA stability; phosphorylation or dephosphorylation; nuclease activity; identification of downstream or reporter gene expression (CAT, luciferase, β-gal, GFP and the like), e.g., via chemiluminescence, fluorescence, colorimetric reactions, antibody binding, and inducible markers.

"Inhibitors", "activators", and "modulators" of MRE11 polynucleotide and polypeptide sequences are used to refer to activating, inhibitory, or modulating molecules identified using in vitro and in vivo assays of MRE11 polynucleotide and polypeptide sequences. Inhibitors are compounds that, e.g., bind to, partially or totally block activity, decrease, prevent, delay activation, inactivate, desensitize, or down regulate the activity or expression of MRE11 proteins, e.g., antagonists. "Activators" are compounds that increase, open, activate, facilitate, enhance activation, sensitize, agonize, or up regulate MRE11 protein activity, e.g., agonists. Inhibitors, activators, or modulators also include genetically modified versions of MRE11 proteins, e.g., versions with altered activity, as well as naturally occurring and synthetic ligands, substrates, antagonists, agonists, antibodies, peptides, cyclic peptides, nucleic acids, antisense molecules, ribozymes, RNAi, small chemical molecules and the like. Such assays for inhibitors and activators include, e.g., expressing MRE11 protein in vitro, in cells, or cell membranes, applying putative modulator compounds, and then determining the functional effects on activity, as described above.

Samples or assays comprising MRE11 proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of MRE11 is achieved when the activity value relative to the control is about 80%, preferably 50%, more preferably 25-0%. Activation of MRE11 is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence SEQ ID NO:1 or amino acid sequence SEQ ID NO:2), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a nuclease domain. Typical domains are made up of sections of lesser organization such as stretches of η-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2-5 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Trau-necker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a MRE11 protein, polymorphic variants, alleles, orthologs, and conservatively modified variants, or splice variants, or portions thereof, can be selected to obtain only those polyclonal antibodies that are specifically immunoreactive with MRE11 proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

Assays for Protiens that Modulation Cellular Proliferarion

High throughput functional genomics assays can be used to identify modulators of cellular proliferation. Such assays can monitor changes in cell surface marker expression, proliferation and differentiation, and apoptosis, using either cell lines or primary cells. Typically, the cells are contacted with a cDNA or a random peptide library (encoded by nucleic acids). In one embodiment, the peptides are cyclic or circular. The cDNA library can comprise sense, antisense, full length, and truncated cDNAs. The peptide library is encoded by nucleic acids. The effect of the cDNA or peptide library on the phenotype of cellular proliferation is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., MRE11) can be isolated using a yeast two-hybrid system, mammalian two hybrid system, immunoprecipitation or affinity chromatography of complexed proteins followed by mass spectrometry, or phage display screen, etc. Targets so identified can be further used as bait in these assays to identify additional members of the cellular proliferation pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable cell lines include A549, HeLa, Jurkat, BJAB, Colo205, H1299, MCF7, MDA-MB-231, PC3, HUMEC, HUVEC, and PrEC. Cell surface markers can be assayed using fluorescently labeled antibodies and FACS. Cell proliferation can be measured using $^3$H-thymidine, MTT assay, BrdU incorporation, cell tracker assay, cell count, AlmarBlue assay, or dye inclusion. Apoptosis can be measured using dye inclusion, or by assaying for DNA laddering, increases in intracellular calcium, or caspase activation assay Growth factor production can be measured using an immunoassay such as ELISA.

cDNA libraries are made from any suitable source. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

Isolation of Nucleic Acids Encoding MRE11 Family Members

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

MRE11 nucleic acids, polymorphic variants, orthologs, and alleles that are substantially identical to an amino acid sequence encoded by SEQ ID NO:2 can be isolated using MRE11 nucleic acid probes and oligonucleotides under stringent hybridization conditions, by screening libraries. Alternatively, expression libraries can be used to clone MRE11 protein, polymorphic variants, orthologs, and alleles by detecting expressed homologs immunologically with antisera or purified antibodies made against human MRE11 or portions thereof.

To make a cDNA library, one should choose a source that is rich in MRE11 RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA*, 72:3961-3965 (1975).

An alternative method of isolating MRE11 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human MRE11 directly from mRNA, from cDNA, from genomic libraries or cDNA libraries. Degenerate oligonucleotides can be designed to amplify MRE11 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of MRE11 encoding mRNA in physiological samples, for nucleic acid sequencing, or for other purposes. Genes amplified by the PCR reaction can be purified from agarose gels and cloned into an appropriate vector.

Gene expression of MRE11 can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology, e.g., and the like.

Nucleic acids encoding MRE11 protein can be used with high density oligonucleotide array technology (e.g., GeneChip™) to identify MRE11 protein, orthologs, alleles, conservatively modified variants, and polymorphic variants in this invention. In the case where the homologs being identified are linked to modulation of cellular proliferation, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene for MRE11 is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding MRE11, one typically subclones MRE11 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the MRE11 protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the MRE11 encoding nucleic acid in host cells. A typical expression cassette thus contains a promoter operably linked to the nucleic acid sequence encoding MRE11 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a MRE11 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of MRE11 protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing MRE11.

After the expression vector is introduced into the cells, the transfected cells are cultured under conditions favoring expression of MRE11, which is recovered from the culture using standard techniques identified below.

Purifacation of MRE11 Polypeptides

Either naturally occurring or recombinant MRE11 can be purified for use in functional assays. Naturally occurring MRE11 can be purified, e.g., from human tissue. Recombinant MRE11 can be purified from any suitable expression system, such as bacteria, yeast, plants, insects, and mammalian cells.

The MRE11 protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant MRE11 protein is being purified. For example, proteins having established molecular adhesion properties can be reversible fused to the MRE11 protein. With the appropriate ligand (e.g., binding partners such as RAD50 and NBS1) or substrate, MRE11 protein can be selectively adsorbed to a purification column and then freed from the column in a relatively pure form. The fused protein is then removed by enzymatic activity. Finally, MRE11 protein could be purified using immunoaffinity columns.

A. Purification of MRE11 from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of MRE11 protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human MRE11 proteins are separated from other bacterial proteins by standard separation techniques, e.g., with Ni-NTA agarose resin.

Alternatively, it is possible to purify MRE11 protein from bacteria periplasm. After lysis of the bacteria, when the MRE11 protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying MRE11 Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the MRE11 proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The MRE11 proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of MRE11 Protein

A. Assays

Modulation of an MRE11 protein, and corresponding modulation of cellular, e.g., tumor cell, proliferation, can be assessed using a variety of in vitro and in vivo assays, including cell-based models. Such assays can be used to test for inhibitors and activators of MRE11 protein, and, consequently, inhibitors and activators of cellular proliferation, including modulators of chemotherapeutic sensitivity and toxicity. Such modulators of MRE11 protein are useful for treating disorders related to pathological cell proliferation, e.g., cancer. Modulators of MRE11 protein are tested using either recombinant or naturally occurring MRE11, preferably human MRE11.

Preferably, the MRE11 protein will have the sequence as encoded by SEQ ID NO:2 or a conservatively modified variant thereof. Alternatively, the MRE11 protein of the assay will be derived from a eukaryote and include an amino acid subsequence having substantial amino acid sequence identity to SEQ ID NO:2. Generally, the amino acid sequence identity will be at least 60%, preferably at least 65%, 70%, 75%, 80%, 85%, or 90%, most preferably at least 95%.

Measurement of cellular proliferation modulation with MRE11 protein or a cell expressing MRE11 protein, either recombinant or naturally occurring, can be performed using a variety of assays, in vitro, in vivo, and ex vivo, as described herein. A suitable physical, chemical or phenotypic change that affects activity, e.g., enzymatic activity (endo- and exonuclease activity for ds and ss nucleic acid), cell proliferation, substrate binding (ds or ss nucleic acid) or ligand binding (e.g., RAD50) can be used to assess the influence of a test compound on the polypeptide of this invention. When the functional effects are determined using intact cells or animals, one can also measure a variety of effects, such as, ligand binding, substrate binding, endonuclease and/or exonuclease activity, transcriptional changes to both known and uncharacterized genetic markers (e.g., northern blots), changes in cell metabolism, changes related to cellular proliferation, cell surface marker expression, DNA synthesis, marker and dye dilution assays (e.g., GFP and cell tracker assays), contact inhibition, tumor growth in nude mice, etc.

In Vitro Assays

Figure 28:
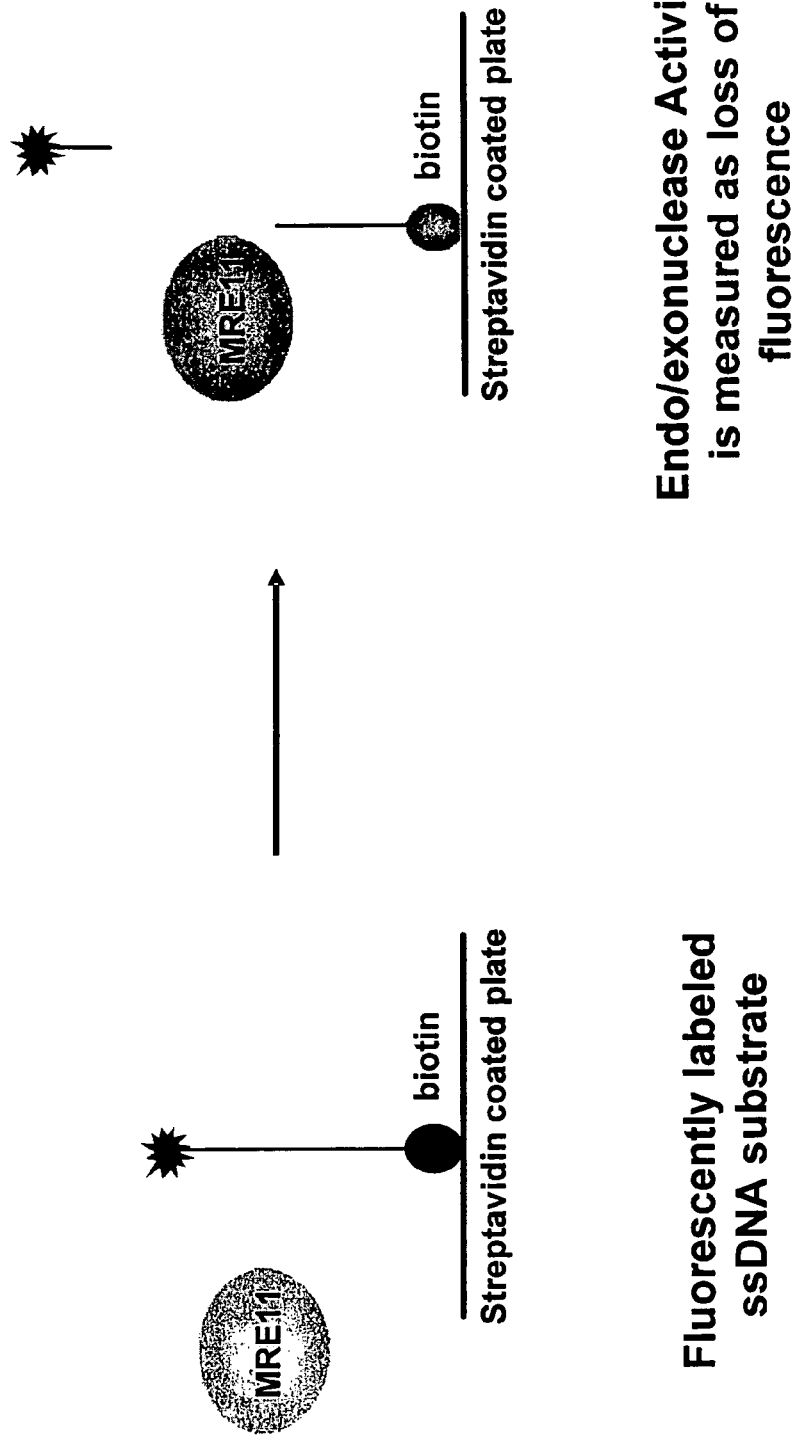
FIG. 28 shows a proposed HTS compatible biochemical assay for MRE11.

Assays to identify compounds with MRE11 modulating activity can be performed in vitro (e.g., biochemical assays). FIG. 28 shows one example of a high throughput biochemical assay for exonuclease activity (see also FIGS. 29-33). Assays for endonuclease activity are also useful. Enzymatic or biochemical assays include biotinylated substrates non-covalently bound to a plate, and labeled with a fluorescent molecule; measurement of BrdU bound to substrate, using an anti-Brdu-HRP antibody; dye binding (e.g., picogreen dye); and fluorescence quenching. The MRE11 substrate can be a synthetic or recombinant oligonucleotide or nucleic acid, either single-stranded or double stranded, or DNA from a cell, either single or double stranded. The DNA can be labeled or unlabeled.

Such assays can used full length MRE11 protein or a variant thereof (see, e.g., SEQ ID NO:2), or a fragment of an MRE11 protein, such as a nuclease domain. Purified recombinant or naturally occurring MRE11 protein can be used in the in vitro methods of the invention. In addition to purified MRE11 protein, the recombinant or naturally occurring MRE11 protein can be part of a cellular lysate, nuclear extract, or a cell membrane.

Ligand and substrate binding assays can also be performed. As described below, the biochemical assay can be either solid state or soluble. For the biochemical assays, the protein, substrate (e.g., ss or ds nucleic acid) or ligand is bound to a solid support, either covalently or non-covalently. Often, the in vitro assays of the invention are ligand binding or ligand affinity assays, either non-competitive or competitive (with a ligand such as RAD50 or NBS1), or substrate binding and enzymatic activity assays, such as endo- and exo-nuclease assays. Other in vitro assays include measuring changes in spectroscopic (e.g., fluorescence, absorbance, refractive index), hydrodynamic (e.g., shape), chromatographic, or solubility properties for the protein.

In one embodiment, a high throughput assay is performed in which the MRE11 protein or a fragment thereof in the biochemical assay is contacted with a potential modulator and incubated for a suitable amount of time, e.g., with. In one embodiment, the potential modulator is bound to a solid support, and the MRE11 protein is added. In another embodiment, the MRE11 protein is bound to a solid support. A wide variety of modulators can be used, as described below, including small organic molecules, peptides, antibodies, and MRE11 ligand analogs. A wide variety of assays can be used to identify MRE11-modulator binding, including enzymatic activity assays (endo- or exonuclease assays) labeled protein-protein binding assays, electrophoretic mobility shifts, immunoassays, and the like.

In some cases, the binding of the candidate modulator is determined through the use of competitive binding assays, where interference with binding of a known ligand or substrate is measured in the presence of a potential modulator. Either the modulator or the known ligand is bound first, and then the competitor is added. After the MRE11 protein is washed, interference with binding, either of the potential modulator or of the known ligand, is determined. Often, either the potential modulator or the known ligand is labeled.

Cell-based in Vivo Assays

In another embodiment, MRE11 protein is expressed in a cell, and functional, e.g., physical and chemical or phenotypic, changes are assayed to identify MRE11 and modulators of cellular proliferation, e.g., tumor cell proliferation. Cells expressing MRE11 proteins can also be used in binding assays and enzymatic assays. Any suitable functional effect can be measured, as described herein. For example, cellular morphology (e.g., cell volume, nuclear volume, cell perimeter, and nuclear perimeter), ligand binding, substrate binding, nuclease activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoescht dye with FACS analysis) and nuclear foci assays, are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), HeLa (cervical), PC3 (prostate, p53 mutant), MDA-MB-231 (breast, p53 wild-type). Cancer cell lines can be p53 mutant, p53 null, or express wild type p53. The MRE11 protein can be naturally occurring or recombinant. Also, fragments of MRE11 or chimeric MRE11 proteins with nuclease activity can be used in cell based assays.

Cellular MRE11 polypeptide levels can be determined by measuring the level of protein or mRNA. The level of MRE11 protein or proteins related to MRE11 are measured using immunoassays such as western blotting, ELISA and the like with an antibody that selectively binds to the MRE11 polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, MRE11 expression can be measured using a reporter gene system. Such a system can be devised using an MRE11 protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)).

The reporter construct is typically transfected into a cell. After treatment with a potential modulator, the amount of reporter gene transcription, translation, or activity is measured according to standard techniques known to those of skill in the art.

Animal Models

Animal models of cellular proliferation also find use in screening for modulators of cellular proliferation, e.g., inhibitors of MRE11. Similarly, transgenic animal technology including gene knockout technology, for example as a result of homologous recombination with an appropriate gene targeting vector, or gene overexpression, will result in the absence or increased expression of the MRE11 protein. The same technology can also be applied to make knock-out cells. When desired, tissue-specific expression or knockout of the MRE11 protein may be necessary. Transgenic animals generated by such methods find use as animal models of cellular proliferation and are additionally useful in screening for modulators of cellular proliferation.

Knock-out cells and transgenic mice can be made by insertion of a marker gene or other heterologous gene into an endogenous MRE11 gene site in the mouse genome via homologous recombination. Such mice can also be made by substituting an endogenous MRE11 with a mutated version of the MRE11 gene, or by mutating an endogenous MRE11, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Exemplary Assays

Biochemical Assays

Figure 29:
FIG. 29 shows an oligonucleotide duplex substrate (SEQ ID NOS:19 and 20) for MRE11 plate-based assay.
Figure 30:
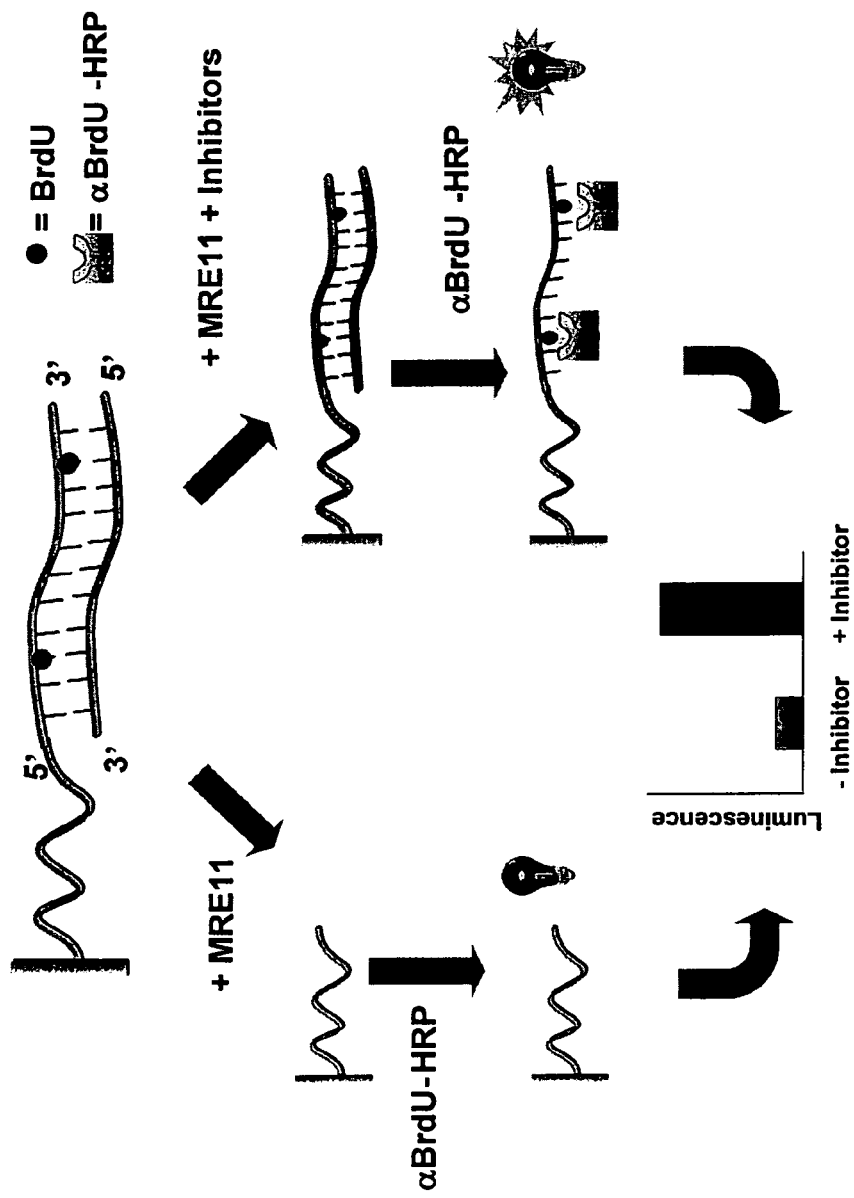
FIG. 30 shows a biochemical assay for MRE11 exonuclease activity.
Figure 31:
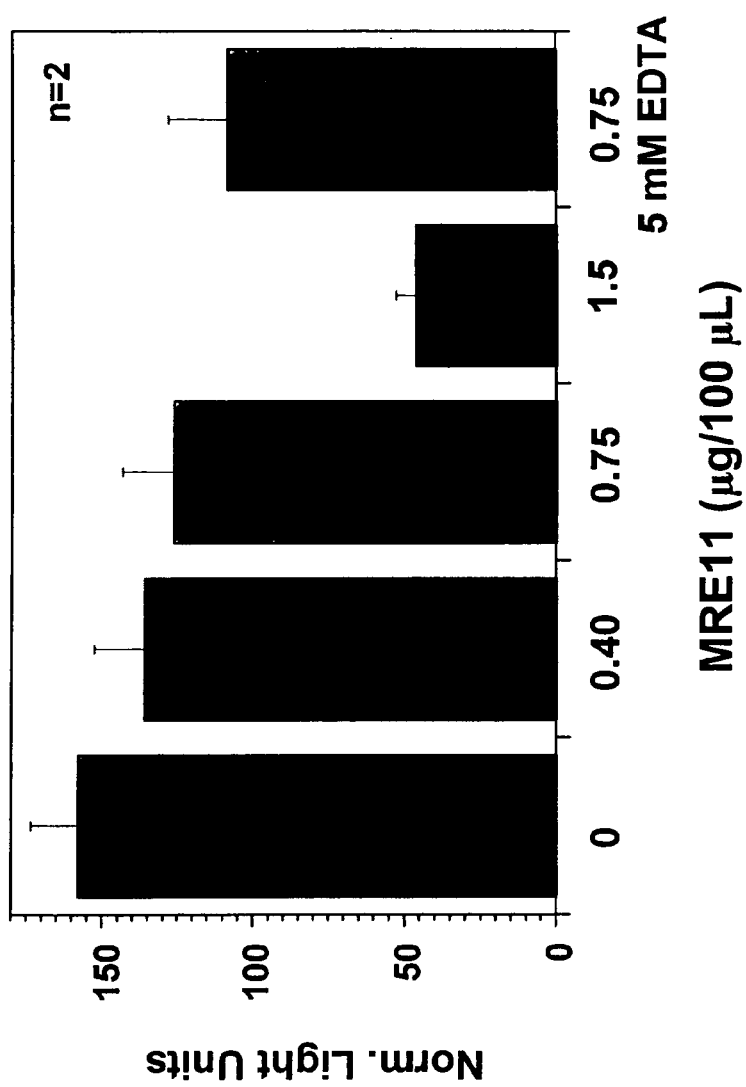
FIG. 31 shows cleavage of double-stranded biotinylated reporter by MRE11.
Figure 32:
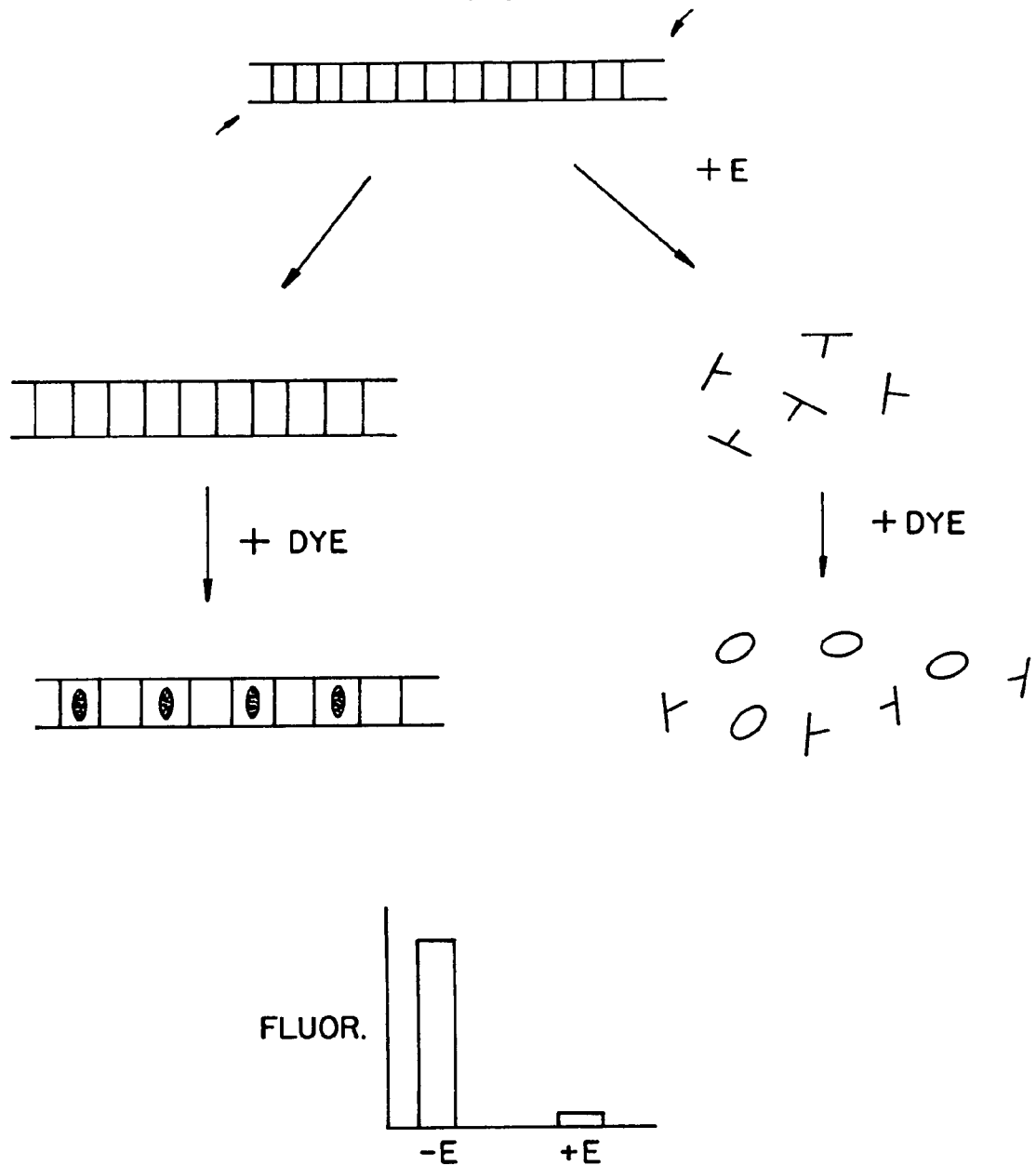
FIG. 32 shows a picogreen dye assay.
Figure 33:
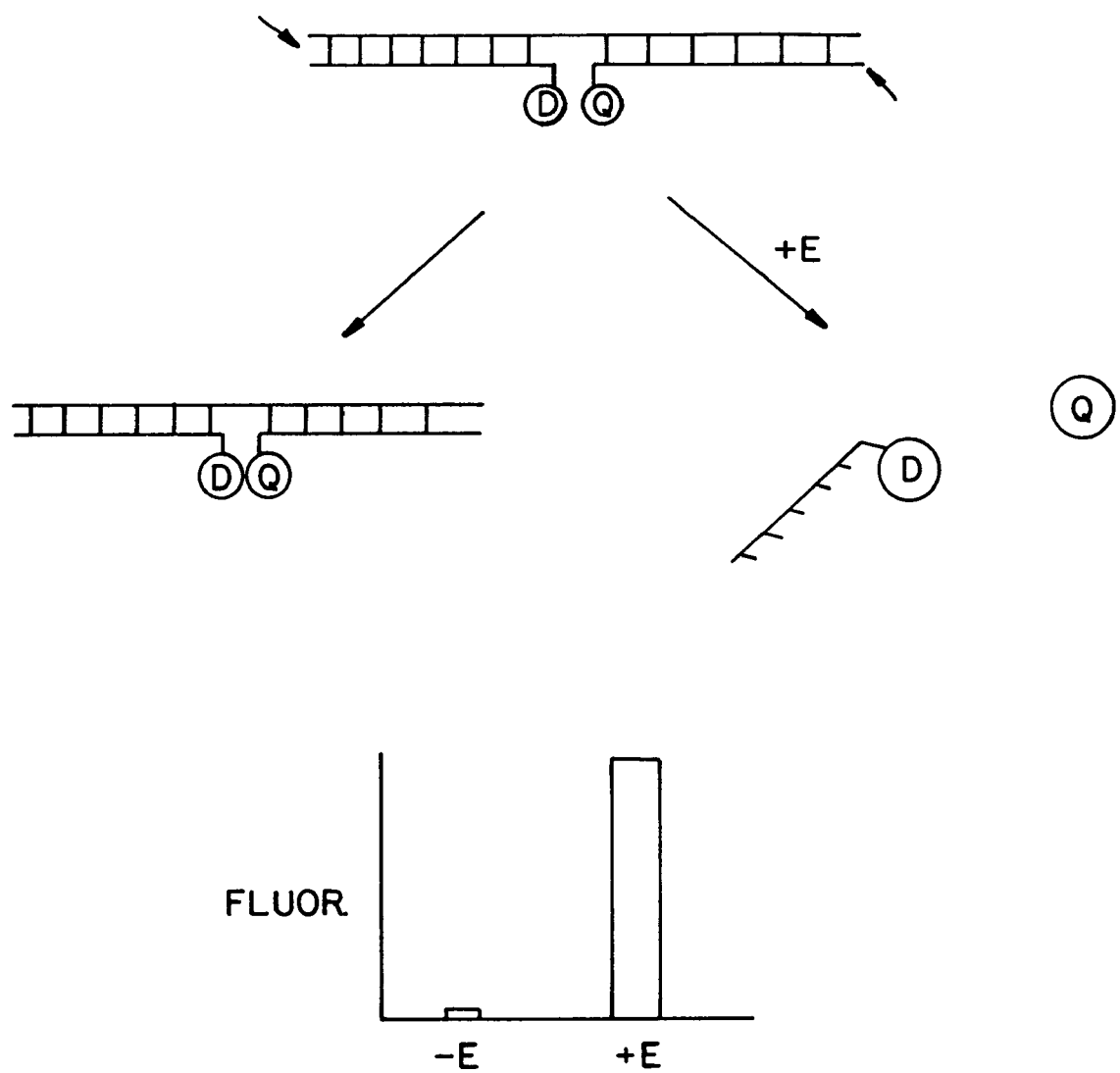
FIG. 33 shows fluorescence quenching assays.

Exemplary biochemical assays are described in FIGS. 28 and 30-31. One assay uses a heterogenous assay format with chemiluminescent readout. This assay relies upon the differential activity of anti-BrdU against an immobilized oligonucleotide substrate containing the antigen (BrdU). The exonuclease activity of MRE11 results in the release of BrdU from the immobilized strand, leading to loss of signal when the MRE11-treated strand is incubated with HRP-conjugated anti-BrdU followed by incubation with a chemiluminescent HRP substrate (FIGS. 29-31).

Another biochemical assay is a homogenous assay format with a fluorescent readout. This assay is based on the difference in fluorescence of a special dye in the presence of nucleic acids. The fluorescence enhancement of the dye upon binding to double-stranded DNA is greater than 1000-fold over the background fluorescence of the dye itself (or in the presence of nucleotides). The exonuclease activity of MRE11 results in the digestion of a 40-mer duplex oligonucleotide into free nucleotides, causing a dramatic decrease in the fluorescent intensity of the dye (see FIG. 32).

Another biochemical assay is a homogenous assay format based on fluorescent quenching, based on a change in the structural integrity of an oligonucleotide duplex containing a donor fluorophore positioned next to a quencher molecule. When the duplex is intact (in the absence of MRE11), the donor and quencher are held in close spatial proximity, resulting in quenching of the fluorescent donor. Exonuclease activity of MRE11 results in digestion of the duplex, leading to the physical separation of the fluorescent donor and quencher and an accompanying increase in the fluorescence of the donor (see FIG. 33).

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify MRE11 modulators. Typically, transformed host cells (e.g., cells that grow on soft agar) are used in this assay. For example, RKO or HCT116 cell lines can be used. Techniques for soft agar growth or colony formation in suspension assays are described in Freshney, *Culture of Animal Cells a Manual of Basic Technique*, 3$^{rd}$ ed., Wiley-Liss, New York (1994), herein incorporated by reference. See also, the methods section of Garkavtsev et al. (1996), supra, herein incorporated by reference.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mihich (ed.): "Biological Responses in Cancer." New York, Academic Press, pp. 178-184 (1985)). Similarly, tumor angiogenesis factor (TAF) is released at a higher level in tumor cells than their normal counterparts. See, e.g., Folkman, Angiogenesis and cancer, *Sem Cancer Biol.* (1992)).

Tumor specific markers can be assayed to identify MRE11 modulators which decrease the level of release of these markers from host cells. Typically, transformed or tumorigenic host cells are used. Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305-312 (1980); Gulino, *Angiogenesis, tumor vascularization, and potential interference with tumor growth.* In Mihich, E. (ed): "Biological Responses in Cancer." New York, Plenum (1985); Freshney *Anticancer Res.* 5:111-130 (1985).

Invasiveness into Matrigel

The degree of invasiveness into Matrigel or some other extracellular matrix constituent can be used as an assay to identify MRE11 modulators which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Therefore, MRE11 modulators can be identified by measuring changes in the level of invasiveness between the host cells before and after the introduction of potential modulators. If a compound modulates MRE11, its expression in tumorigenic host cells would affect invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}I$ and counting the radioactivity on the distal side of the filter or bottom of the dish. See, e.g., Freshney (1984), supra.

Apoptosis Analysis

Apoptosis analysis can be used as an assay to identify MRE11 modulators. In this assay, cell lines, such as RKO or HCT116, can be used to screen MRE11 modulators. Cells are contacted with a putative MRE11 modulator. The cells can be co-transfected with a construct comprising a marker gene, such as a gene that encodes green fluorescent protein, or a cell tracker dye. The apoptotic change can be determined using methods known in the art, such as DAPI staining and TUNEL assay using fluorescent microscope. For TUNEL assay, commercially available kit can be used (e.g., Fluorescein FragEL DNA Fragmentation Detection Kit (Oncogene Research Products, Cat.# QIA39)+Tetramethyl-rhodamine-5-dUTP (Roche, Cat. # 1534 378)). Cells contacted with MRE11 modulators would exhibit, e.g., an increased apoptosis compared to control.

$G_0/G_1$ Cell Cycle Arrest Analysis $G_0/G_1$ cell cycle arrest can be used as an assay to identify MRE11 modulators. In this assay, cell lines, such as RKO or HCT116, can be used to screen MRE11 modulators. The cells can be co-transfected with a construct comprising a marker gene, such as a gene that encodes green fluorescent protein, or a cell tracker dye. Methods known in the art can be used to measure the degree of $G_1$ cell cycle arrest. For example, a propidium iodide signal can be used as a measure for DNA content to determine cell cycle profiles on a flow cytometer. The percent of the cells in each cell cycle can be calculated. Cells contacted with a MRE11 modulator would exhibit, e.g., a higher number of cells that are arrested in $G_0/G_1$ phase compared to control.

Tumor Growth in Vivo

Effects of MRE11 modulators on cell growth can be tested in transgenic or immune-suppressed mice. Knock-out transgenic mice can be made, in which the endogenous MRE11 gene is disrupted. Such knock-out mice can be used to study effects of MRE11, e.g., as a cancer model, as a means of assaying in vivo for compounds that modulate MRE11, and to test the effects of restoring a wild-type or mutant MRE11 to a knock-out mice.

Knock-out cells and transgenic mice can be made by insertion of a marker gene or other heterologous gene into the endogenous MRE11 gene site in the mouse genome via homologous recombination. Such mice can also be made by substituting the endogenous MRE11 with a mutated version of MRE11, or by mutating the endogenous MRE11, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987). These knock-out mice can be used as hosts to test the effects of various MRE11 modulators on cell growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. Hosts are treated with MRE11 modulators, e.g., by injection. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, MRE11 modulators which are capable, e.g., of inhibiting abnormal cell proliferation can be identified.

B. Modulators

The compounds tested as modulators of MRE11 protein can be any small organic molecule, or a biological entity, such as a protein, e.g., an antibody or peptide, a sugar, a nucleic acid, e.g., an antisense oligonucleotide, RNAi, or a ribozyme, or a lipid. Alternatively, modulators can be genetically altered versions of an MRE11 protein. Typically, test compounds will be small organic molecules, peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libranes" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274: 1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a MRE11 protein, or a cell or tissue expressing an MRE11 protein, either naturally occurring or recombinant. In another embodiment, the invention provides solid phase based in vitro assays in a high throughput format, where the MRE11 protein its substrate is attached to a solid phase substrate via covalent or non-covalent interactions. Any one of the assays described herein can be adapted for high throughput screening.

In the high throughput assays of the invention, either soluble or solid state, it is possible to screen up to several thousand different modulators or ligands in a single day. This methodology can be used for MRE11 proteins in vitro, or for cell-based or membrane-based assays comprising an MRE11 protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA hnmunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:21). Such flexible linkers are known to persons of skill in the art. For example, poly (ethylene glycol) linkers are available from Shearwater Polymers, Inc., Huntsville, Ala. These linkers optionally have amide linkages, sulfhydryl linkges, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins; Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of MRE11 Polypeptides

In addition to the detection of MRE11 gene and gene expression using nucleic acid hybridization technology, one can also use immunoassays to detect MRE11 proteins of the invention. Such assays are useful for screening for modulators of MRE11, as well as for therapeutic and diagnostic applications. Immunoassays can be used to qualitatively or quantitatively analyze MRE11 protein. A general overview of the applicable technology can be found in Harlow & Lane, *Antibodies: A Laboratory Manual* (1988).

A. Production of Antibodies

Methods of producing polyclonal and monoclonal antibodies that react specifically with the MRE11 proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of MRE11 protein may be used to produce antibodies specifically reactive with MRE11 protein. For example, recombinant MRE11 protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J Immunol.* 6:511b-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non- MRE11 proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular MRE11 ortholog, such as human MRE11, can also be made, by subtracting out other cross-reacting orthologs from a species such as a nonhuman mammal. In this manner, antibodies that bind only to MRE11 protein may be obtained.

Once the specific antibodies against MRE11 protein are available, the protein can be detected by a variety of immunoassay methods. In addition, the antibody can be used therapeutically as a MRE11 modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

MRE11 protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the MRE11 protein or antigenic subsequence thereof). The antibody (e.g., anti-MRE11) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled MRE11 or a labeled anti-MRE11 antibody. Alternatively, the labeling agent may be a third moiety, such a secondary antibody, that specifically binds to the antibody/MRE11 complex (a secondary antibody is typically specific to antibodies of the species from which the first antibody is derived). Other proteins capable of specifically binding immunoglobulin constant regions, such as protein A or protein G may be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting MRE11 in samples may be either competitive or noncompetitive. Noncompetitive immunoassays are assays in which the amount of antigen is directly measured. In one preferred "sandwich" assay, for example, the anti-MRE11 antibodies can be bound directly to a solid substrate on which they are immobilized. These immobilized antibodies then capture MRE11 present in the test sample. MRE11 proteins thus immobilized are then bound by a labeling agent, such as a second MRE11 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of MRE11 protein present in the sample is measured indirectly by measuring the amount of a known, added (exogenous) MRE11 protein displaced (competed away) from an anti-MRE11 antibody by the unknown MRE11 protein present in a sample. In one competitive assay, a known amount of MRE11 protein is added to a sample and the sample is then contacted with an antibody that specifically binds to MRE11 protein. The amount of exogenous MRE11 protein bound to the antibody is inversely proportional to the concentration of MRE11 protein present in the sample. In a particularly preferred embodiment, the antibody is immobilized on a solid substrate. The amount of MRE11 protein bound to the antibody may be determined either by measuring the amount of MRE11 present in MRE11 protein/antibody complex, or alternatively by measuring the amount of remaining uncomplexed protein. The amount of MRE11 protein may be detected by providing a labeled MRE11 molecule.

A hapten inhibition assay is another preferred competitive assay. In this assay the known MRE11 protein is immobilized on a solid substrate. A known amount of anti-MRE11 antibody is added to the sample, and the sample is then contacted with the immobilized MRE11. The amount of anti-MRE11 antibody bound to the known immobilized MRE11 is inversely proportional to the amount of MRE11 protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, an MRE11 protein can be immobilized to a solid support. Proteins (e.g., MRE11 and homologs) are added to the assay that compete for binding of the antisera to the immobilized antigen. The ability of the added proteins to compete for binding of the antisera to the immobilized protein is compared to the ability of the MRE11 protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an MRE11 protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the MRE11 protein that is required to inhibit 50% of binding, then the second protein is said to specifically bind to the polyclonal antibodies generated to MRE11 immunogen.

Other Assay Formats

Western blot (immunoblot) analysis is used to detect and quantify the presence of MRE11 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind MRE11. The anti-MRE11 antibodies specifically bind to the MRE11 on the solid support. These antibodies may be directly labeled or alternatively may be subsequently detected using labeled antibodies (e.g., labeled sheep anti-mouse antibodies) that specifically bind to the anti-MRE11 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-specific Binding

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), chemiluminescent labels, and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize MRE11 protein, or secondary antibodies that recognize anti-MRE11.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of MRE11 protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a MRE11 protein of the present invention, thereby mitigating the effects of absent, partial inactivation, or abnormal expression of an MRE11 gene, particularly as it relates to cell cycle proliferation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfier & Böhm eds., 1995); and Yu et al., *Gene Therapy* 1:13-26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17th ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the MRE11 protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of MRE11 Using a Yeast Two Hybrid Assay and Role of MRE11 in Modulation of Cellular and Tumor Cell Proliferation MRE11 was identified as a member of the PCNA complex using a yeast two hybrid assay, with PCNA as bait. Proteins interacting with the bait peptide are isolated using yeast two-hybrid systems or mammalian two hybrid systems known to those of skill in the art (see, e.g., Fields et al., *Nature* 340:245 (1989); Vasavada et al., *PNAS USA* 88:10686 (1991); Fearon et al., *PNAS USA* 89:7958 (1992); Dang et al., *Mol. Cell. Biol.* 11:954 (1991); Chien et al., *PNAS USA* 9578 (1991); and U.S. Pat. Nos. 5,283,173, 5,667,973, 5,468,614, 5,525,490, and 5,637,463)

As shown in FIGS. 8-15, studies show that inhibition of MRE11 or overexpression of an MRE11 mutant is antiproliferative in A549 tumor cells and HeLa cells but not in normal cells (using, e.g., GFP positivity assays, cell tracker assays, and antisense assays). FIGS. 16-22 demonstrate that overexpression of an MRE11 mutant enhances sensitivity to chemotherapeutic reagents in tumor cells. These functional studies demonstrate that inhibition of MRE11 will inhibit tumor cell growth and enhance chemosensitivity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for identifying a compound that modulates cellular proliferation or chemosensitivity, the method comprising the steps of contacting the compound with a meiotic recombination 11 (MRE11) polypeptide, wherein the polypeptide has at least about 95% amino acid sequence identity to SEQ ID NO:2 and has nuclease activity, and determining a functional effect of said compound by measuring nuclease activity of the MRE11 polypeptide, wherein an effect of said compound on the nuclease activity of said MRE11 polypeptide indicates that said compound modulates cellular proliferation or chemosensitivity.

2. The method of claim 1, wherein the MRE11 polypeptide is expressed in a eukaryotic host cell.

3. The method of claim 1, wherein modulation is inhibition of cellular proliferation.

4. The method of claim 1, wherein modulation is inhibition of cancer cell proliferation.

5. The method of claim 1, wherein modulation is activating sensitivity to chemotherapeutic reagents.

6. The method of claim 1, wherein modulation is activating sensitivity of cancer cells to chemotherapeutic reagents.

7. The method of claim 2, wherein the host cell is a cancer cell.

8. The method of claim 7, wherein the cancer cell is a breast, prostate, colon, or lung cancer cell.

9. The method of claim 7, wherein the cancer cell is a transformed cell line.

10. The method of claim 9, wherein the transformed cell line is PC3, HI299, MDA-MB-231, MCF7, A549, or HeLa.

11. The method of claim 7, wherein the cancer cell is a p53 null or mutant cell.

12. The method of claim 7, wherein the cancer cell is a p53 wild-type cell.

13. The method of claim 7, wherein the cancer cell is treated with bleomycin or etoposide.

14. The method of claim 1, wherein the polypeptide is recombinant.

15. The method of claim 1, wherein the polypeptide is encoded by a nucleic acid having the sequence of SEQ ID NO: 1.

16. The method of claim 1, wherein the compound is an antibody.

17. The method of claim 1, wherein the compound is an antisense molecule.

18. The method of claim 1, wherein the compound is a small organic molecule.

19. The method of claim 1, wherein the compound is a peptide.

20. The method of claim 19, wherein the peptide is circular.

21. The method of claim 1, wherein the MRE11 polypeptide has the amino acid sequence of SEQ ID NO:2.

22. The method of claim 1, wherein the MRE11 polypeptide is encoded by a nucleic acid sequence having at least about 95% nucleic acid sequence identity to SEQ ID NO: 1.

* * * * *

```
                          SEQUENCE LISTING

<160> NUMBER OF SEQ ID NOS: 21

<210> SEQ ID NO 1
<211> LENGTH: 2537
<212> TYPE: DNA
<213> ORGANISM: Homo sapiens
<220> FEATURE:
<223> OTHER INFORMATION: human MRE11 meiotic recombination 11 homolog A
<220> FEATURE:
<221> NAME/KEY: CDS
<222> LOCATION: (171)..(2297)
<223> OTHER INFORMATION: MRE11

<400> SEQUENCE: 1
ccacgcgtcc gggacgccgt tctctcccgc ggaattcagg tttacggccc tgcgggttct      60
cagagaattt ctagaatttg gaatcgagtg cattttctga catttgagta cagtacccag     120
gggttcttgg agaagaacct ggtcccagag gagcttgact gaccataaaa atgagtactg     180
cagatgcact tgatgatgaa aacacattta aaatattagt tgcaacagat attcatcttg     240
gatttatgga gaaagatgca gtcagaggaa atgatacgtt tgtaacactc gatgaaattt     300
taagacttgc ccaggaaaat gaagtggatt ttattttgtt aggtggtgat ctttttcatg     360
aaaataagcc ctcaaggaaa acattacata cctgcctcga gttattaaga aaatattgta     420
tgggtgatcg gcctgtccag tttgaaattc tcagtgatca gtcagtcaac tttggtttta     480
gtaagtttcc atgggtgaac tatcaagatg caacctcaa  catttcaatt ccagtgttta     540
gtattcatgg caatcatgac gatcccacag gggcagatgc actttgtgcc ttggacattt     600
taagttgtgc tggatttgta aatcactttg gacgttcaat gtctgtggag aagatagaca     660
ttagtccggt tttgcttcaa aaaggaagca caaagattgc gctatatggt ttaggatcca     720
ttccagatga aaggctctat cgaatgtttg tcaataaaaa agtaacaatg ttgagaccaa     780
aggaagatga gaactcttgg tttaacttat ttgtgattca tcagaacagg agtaaacatg     840
gaagtactaa cttcattcca gaacaatttt tggatgactt cattgatctt gttatctggg     900
gccatgaaca tgagtgtaaa atagctccaa ccaaaaatga caacagctg  tttttatatct     960 cacaacctgg aagctcagtg gttacttctc tttccccagg agaagctgta aagaaacatg    1020
ttggtttgct gcgtattaaa gggaggaaga tgaatatgca taaattcct cttcacacag     1080 tgcggcagtt tttcatggag gatattgttc tagctaatca tccagacatt tttaacccag    1140
ataatcctaa agtaacccaa gccatacaaa gcttctgttt ggagaagatt gaagaaatgc    1200
ttgaaaatgc tgaacgggaa cgtctgggta ttctcacca gccagagaag cctcttgtac    1260
gactgcgagt ggactatagt ggaggtttg  aacctttcag tgttcttcgc tttagccaga    1320
aatttgtgga tcgggtagct aatccaaaag acattatcca ttttttcagg catagagaac    1380
aaaaggaaaa aacaggagaa gagatcaact ttgggaaact tatcacaaag ccttcagaag    1440
gaacaacttt aagggtagaa gatcttgtaa aacagtactt tcaaaccgca gagaagaatg    1500
tgcagctctc actgctaaca gaaagaggga tgggtgaagc agtacaagaa tttgtggaca    1560
aggagggaaa agatgccatt gaggaattag tgaaatacca gttggaaaaa acacagcgat    1620
ttcttaaaga acgtcatatt gatgccctcg aagacaaaat cgatgaggag gtacgtcgtt    1680
```

-continued

```
tcagagaaac cagacaaaaa aatactaatg aagaagatga tgaagtccgt gaggctatga    1740
ccagggccag agcactcaga tctcagtcag aggagtctgc ttctgccttt agtgctgatg    1800
accttatgag tatagattta gcagaacaga tggctaatga ctctgatgat agcatctcag    1860
cagcaaccaa caaaggaaga ggccgaggaa gaggtcgaag aggtggaaga gggcagaatt    1920
cagcatcgag aggagggtct caaagaggaa gagcagacac tggtctggag acttctaccc    1980
gtagcaggaa ctcaaagact gctgtgtcag catctagaaa tatgtctatt atagatgcct    2040
ttaaatctac aagacagcag ccttcccgaa atgtcactac taagaattat tcagaggtga    2100
ttgaggtaga tgaatcagat gtggaagaag acatttttcc taccacttca aagacagatc    2160
aaaggtggtc cagcacatca tccagcaaaa tcatgtccca gagtcaagta tcgaaagggg    2220
ttgattttga atcaagtgag gatgatgatg atgatccttt tatgaacact agttctttaa    2280
gaagaaatag aagataatat atttaatggc actgagaaac atgcaagata caggaaaaat    2340
gaaaatgtta caagctaaga gtttacagtt taagatttta agtattgttt cctgagcata    2400
actccataag taagaaattt ctagttcaca gacatacaat agcattgatt caccttgttt    2460
ttttaacctg gttgttgtag taagagcttt gtttcaatat cactcttgag taaagattaa    2520
aataaagcta ccatttt                                                   2537
```

<210> SEQ ID NO 2
<211> LENGTH: 708
<212> TYPE: PRT
<213> ORGANISM: Homo sapiens
<220> FEATURE:
<223> OTHER INFORMATION: human MRE11 meiotic recombination 11 homolog A

<400> SEQUENCE: 2

```
Met Ser Thr Ala Asp Ala Leu Asp Asp Glu Asn Thr Phe Lys Ile Leu
  1               5                  10                  15

Val Ala Thr Asp Ile His Leu Gly Phe Met Glu Lys Asp Ala Val Arg
             20                  25                  30

Gly Asn Asp Thr Phe Val Thr Leu Asp Glu Ile Leu Arg Leu Ala Gln
         35                  40                  45

Glu Asn Glu Val Asp Phe Ile Leu Leu Gly Gly Asp Leu Phe His Glu
     50                  55                  60

Asn Lys Pro Ser Arg Lys Thr Leu His Thr Cys Leu Glu Leu Leu Arg
 65                  70                  75                  80

Lys Tyr Cys Met Gly Asp Arg Pro Val Gln Phe Glu Ile Leu Ser Asp
                 85                  90                  95

Gln Ser Val Asn Phe Gly Phe Ser Lys Phe Pro Trp Val Asn Tyr Gln
            100                 105                 110

Asp Gly Asn Leu Asn Ile Ser Ile Pro Val Phe Ser Ile His Gly Asn
        115                 120                 125

His Asp Asp Pro Thr Gly Ala Asp Ala Leu Cys Ala Leu Asp Ile Leu
    130                 135                 140

Ser Cys Ala Gly Phe Val Asn His Phe Gly Arg Ser Met Ser Val Glu
145                 150                 155                 160

Lys Ile Asp Ile Ser Pro Val Leu Leu Gln Lys Gly Ser Thr Lys Ile
                165                 170                 175

Ala Leu Tyr Gly Leu Gly Ser Ile Pro Asp Glu Arg Leu Tyr Arg Met
            180                 185                 190

Phe Val Asn Lys Lys Val Thr Met Leu Arg Pro Lys Glu Asp Glu Asn
        195                 200                 205
```

-continued

Ser Trp Phe Asn Leu Phe Val Ile His Gln Asn Arg Ser Lys His Gly
    210                 215                 220

Ser Thr Asn Phe Ile Pro Glu Gln Phe Leu Asp Asp Phe Ile Asp Leu
225                 230                 235                 240

Val Ile Trp Gly His Glu His Glu Cys Lys Ile Ala Pro Thr Lys Asn
                245                 250                 255

Glu Gln Gln Leu Phe Tyr Ile Ser Gln Pro Gly Ser Ser Val Val Thr
                260                 265                 270

Ser Leu Ser Pro Gly Glu Ala Val Lys Lys His Val Gly Leu Leu Arg
            275                 280                 285

Ile Lys Gly Arg Lys Met Asn Met His Lys Ile Pro Leu His Thr Val
    290                 295                 300

Arg Gln Phe Phe Met Glu Asp Ile Val Leu Ala Asn His Pro Asp Ile
305                 310                 315                 320

Phe Asn Pro Asp Asn Pro Lys Val Thr Gln Ala Ile Gln Ser Phe Cys
                325                 330                 335

Leu Glu Lys Ile Glu Glu Met Leu Glu Asn Ala Glu Arg Glu Arg Leu
                340                 345                 350

Gly Asn Ser His Gln Pro Glu Lys Pro Leu Val Arg Leu Arg Val Asp
            355                 360                 365

Tyr Ser Gly Gly Phe Glu Pro Phe Ser Val Leu Arg Phe Ser Gln Lys
    370                 375                 380

Phe Val Asp Arg Val Ala Asn Pro Lys Asp Ile Ile His Phe Phe Arg
385                 390                 395                 400

His Arg Glu Gln Lys Glu Lys Thr Gly Glu Glu Ile Asn Phe Gly Lys
                405                 410                 415

Leu Ile Thr Lys Pro Ser Glu Gly Thr Thr Leu Arg Val Glu Asp Leu
            420                 425                 430

Val Lys Gln Tyr Phe Gln Thr Ala Glu Lys Asn Val Gln Leu Ser Leu
    435                 440                 445

Leu Thr Glu Arg Gly Met Gly Glu Ala Val Gln Glu Phe Val Asp Lys
450                 455                 460

Glu Glu Lys Asp Ala Ile Glu Glu Leu Val Lys Tyr Gln Leu Glu Lys
465                 470                 475                 480

Thr Gln Arg Phe Leu Lys Glu Arg His Ile Asp Ala Leu Glu Asp Lys
                485                 490                 495

Ile Asp Glu Glu Val Arg Arg Phe Arg Glu Thr Arg Gln Lys Asn Thr
            500                 505                 510

Asn Glu Glu Asp Asp Glu Val Arg Glu Ala Met Thr Arg Ala Arg Ala
    515                 520                 525

Leu Arg Ser Gln Ser Glu Glu Ser Ala Ser Ala Phe Ser Ala Asp Asp
    530                 535                 540

Leu Met Ser Ile Asp Leu Ala Glu Gln Met Ala Asn Asp Ser Asp Asp
545                 550                 555                 560

Ser Ile Ser Ala Ala Thr Asn Lys Gly Arg Gly Arg Gly Arg Gly Arg
                565                 570                 575

Arg Gly Gly Arg Gly Gln Asn Ser Ala Ser Arg Gly Gly Ser Gln Arg
                580                 585                 590

Gly Arg Ala Asp Thr Gly Leu Glu Thr Ser Thr Arg Ser Arg Asn Ser
            595                 600                 605

Lys Thr Ala Val Ser Ala Ser Arg Asn Met Ser Ile Ile Asp Ala Phe
    610                 615                 620

-continued

```
Lys Ser Thr Arg Gln Gln Pro Ser Arg Asn Val Thr Thr Lys Asn Tyr
625                 630                 635                 640

Ser Glu Val Ile Glu Val Asp Glu Ser Asp Val Glu Asp Ile Phe
            645                 650                 655

Pro Thr Thr Ser Lys Thr Asp Gln Arg Trp Ser Ser Thr Ser Ser
                660                 665                 670

Lys Ile Met Ser Gln Ser Gln Val Ser Lys Gly Val Asp Phe Glu Ser
            675                 680                 685

Ser Glu Asp Asp Asp Asp Pro Phe Met Asn Thr Ser Ser Leu Arg
    690                 695                 700

Arg Asn Arg Arg
705

<210> SEQ ID NO 3
<211> LENGTH: 299
<212> TYPE: PRT
<213> ORGANISM: Homo sapiens
<220> FEATURE:
<223> OTHER INFORMATION: human MRE11 amino acids 9-307

<400> SEQUENCE: 3

Asp Glu Asn Thr Phe Lys Ile Leu Val Ala Thr Asp Ile His Leu Gly
1               5                  10                  15

Phe Met Glu Lys Asp Ala Ala Arg Gly Asn Asp Thr Phe Val Thr Leu
            20                  25                  30

Asp Glu Ile Leu Arg Leu Ala Gln Glu Asn Glu Val Asp Phe Ile Leu
        35                  40                  45

Leu Gly Gly Asp Leu Phe His Glu Asn Lys Pro Ser Arg Lys Thr Leu
    50                  55                  60

His Thr Cys Leu Glu Leu Leu Arg Lys Tyr Cys Met Gly Asp Arg Pro
65                  70                  75                  80

Val Gln Phe Glu Ile Leu Ser Asp Gln Ser Val Asn Phe Gly Phe Ser
                85                  90                  95

Lys Phe Pro Trp Val Asn Tyr Gln Asp Gly Asn Leu Asn Ile Ser Ile
            100                 105                 110

Pro Val Phe Ser Ile His Gly Asn His Asp Asp Pro Thr Gly Ala Asp
        115                 120                 125

Ala Leu Cys Ala Leu Asp Ile Leu Ser Cys Ala Gly Phe Val Asn His
    130                 135                 140

Phe Gly Arg Ser Met Ser Val Glu Lys Ile Asp Ile Ser Pro Val Leu
145                 150                 155                 160

Leu Gln Lys Gly Ser Thr Lys Ile Ala Leu Tyr Gly Leu Gly Ser Ile
                165                 170                 175

Pro Asp Glu Arg Leu Tyr Arg Met Phe Val Asn Lys Lys Val Thr Met
            180                 185                 190

Leu Arg Pro Lys Glu Asp Glu Asn Ser Trp Phe Asn Leu Phe Val Ile
        195                 200                 205

His Gln Asn Arg Ser Lys His Gly Ser Thr Asn Phe Ile Pro Glu Gln
    210                 215                 220

Phe Leu Asp Asp Phe Ile Asp Leu Val Ile Trp Gly His Glu His Glu
225                 230                 235                 240

Cys Lys Ile Ala Pro Thr Lys Asn Glu Gln Gln Leu Phe Tyr Ile Ser
                245                 250                 255

Gln Pro Gly Ser Ser Val Val Thr Ser Leu Ser Pro Gly Glu Ala Val
            260                 265                 270
```

```
Lys Lys His Val Gly Leu Leu Arg Ile Lys Gly Arg Lys Met Asn Met
        275                 280                 285

His Lys Ile Pro Leu His Thr Val Arg Gln Phe
        290                 295

<210> SEQ ID NO 4
<211> LENGTH: 300
<212> TYPE: PRT
<213> ORGANISM: Saccharomyces cerevisiae
<220> FEATURE:
<223> OTHER INFORMATION: yeast MRE11 amino acids 5-304

<400> SEQUENCE: 4

Asp Pro Asp Thr Ile Arg Ile Leu Ile Thr Thr Asp Asn His Val Gly
  1               5                  10                  15

Tyr Asn Glu Asn Asp Pro Ile Thr Gly Asp Asp Ser Trp Lys Thr Phe
             20                  25                  30

His Glu Val Met Met Leu Ala Lys Asn Asn Val Asp Met Val Val
         35                  40                  45

Gln Ser Gly Asp Leu Phe His Val Asn Lys Pro Ser Lys Lys Ser Leu
     50                  55                  60

Tyr Gln Val Leu Lys Thr Leu Arg Leu Cys Cys Met Gly Asp Lys Pro
 65                  70                  75                  80

Cys Glu Leu Glu Leu Ser Asp Pro Ser Gln Val Phe His Tyr Asp
                 85                  90                  95

Glu Phe Thr Asn Val Asn Tyr Glu Asp Pro Asn Phe Asn Ile Ser Ile
                100                 105                 110

Pro Val Phe Gly Ile Ser Gly Asn His Asp Asp Ala Ser Gly Asp Ser
            115                 120                 125

Leu Leu Cys Pro Met Asp Ile Leu His Ala Thr Gly Leu Ile Asn His
    130                 135                 140

Phe Gly Lys Val Ile Glu Ser Asp Lys Ile Lys Val Val Pro Leu Leu
145                 150                 155                 160

Phe Gln Lys Gly Ser Thr Lys Leu Ala Leu Tyr Gly Leu Ala Ala Val
                165                 170                 175

Arg Asp Glu Arg Leu Phe Arg Thr Phe Lys Asp Gly Val Thr Phe
                180                 185                 190

Glu Val Pro Thr Met Arg Glu Gly Glu Trp Phe Asn Leu Met Cys Val
            195                 200                 205

His Gln Asn His Thr Gly His Thr Asn Thr Ala Phe Leu Pro Glu Gln
    210                 215                 220

Phe Leu Pro Asp Phe Leu Asp Met Val Ile Trp Gly His Glu His Glu
225                 230                 235                 240

Cys Ile Pro Asn Leu Val His Asn Pro Ile Lys Asn Phe Asp Val Leu
                245                 250                 255

Gln Pro Gly Ser Ser Val Ala Thr Ser Leu Cys Glu Ala Glu Ala Gln
            260                 265                 270

Pro Lys Tyr Val Phe Ile Leu Asp Ile Lys Tyr Gly Glu Ala Pro Lys
        275                 280                 285

Met Thr Pro Ile Pro Leu Glu Thr Ile Arg Thr Phe
    290                 295                 300

<210> SEQ ID NO 5
<211> LENGTH: 5
<212> TYPE: PRT
<213> ORGANISM: Artificial Sequence
<220> FEATURE:
```

```
<223> OTHER INFORMATION: Description of Artificial Sequence:consensus
      MRE11 peptide

<400> SEQUENCE: 5

Gly Asp Leu Phe His
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (5)
<223> OTHER INFORMATION: Xaa = Arg or Lys
<220> FEATURE:
<221> NAME/KEY: MOD_RES
<222> LOCATION: (7)
<223> OTHER INFORMATION: Xaa = Thr or Ser
<220> FEATURE:
<221> NAME/KEY: MOD_RES
<222> LOCATION: (9)
<223> OTHER INFORMATION: Xaa = His or Tyr

<400> SEQUENCE: 6

Asn Lys Pro Ser Xaa Lys Xaa Leu Xaa
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (5)
<223> OTHER INFORMATION: Xaa = Arg or Lys

<400> SEQUENCE: 7

Cys Met Gly Asp Xaa Pro
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (2)
<223> OTHER INFORMATION: Xaa = Ile or Leu

<400> SEQUENCE: 8

Glu Xaa Leu Ser Asp
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:consensus
      MRE11 peptide
```

```
<400> SEQUENCE: 9

Val Asn Tyr Glx Asp
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:consensus
      MRE11 peptide

<400> SEQUENCE: 10

Asn Ile Ser Ile Pro Val Phe
  1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:consensus
      MRE11 peptide

<400> SEQUENCE: 11

Gly Asn His Asp Asp
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (1)
<223> OTHER INFORMATION: Xaa = Val or Ile
<220> FEATURE:
<221> NAME/KEY: MOD_RES
<222> LOCATION: (6)
<223> OTHER INFORMATION: Xaa = Arg or Lys

<400> SEQUENCE: 12

Xaa Asn His Phe Gly Xaa
  1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (7)
<223> OTHER INFORMATION: Xaa = Ile or Leu

<400> SEQUENCE: 13

Gln Lys Gly Ser Thr Lys Xaa Ala Leu Tyr Gly Leu
  1               5                  10

<210> SEQ ID NO 14
<211> LENGTH: 6
<212> TYPE: PRT
<213> ORGANISM: Artificial Sequence
<220> FEATURE:
```

```
<223> OTHER INFORMATION: Description of Artificial Sequence:consensus
      MRE11 peptide
<220> FEATURE:
<221> NAME/KEY: MOD_RES
<222> LOCATION: (5)
<223> OTHER INFORMATION: Xaa = Tyr or Phe

<400> SEQUENCE: 14

Asp Glu Arg Leu Xaa Arg
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:consensus
      MRE11 peptide

<400> SEQUENCE: 15

Trp Phe Asn Leu
 1

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (2)
<223> OTHER INFORMATION: Xaa = Ile or Leu

<400> SEQUENCE: 16

Phe Xaa Pro Glu Gln Phe Leu
 1               5

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence:consensus
      MRE11 peptide
<220> FEATURE:
<221> NAME/KEY: MOD_RES
<222> LOCATION: (3)
<223> OTHER INFORMATION: Xaa = Ile or Leu
<220> FEATURE:
<221> NAME/KEY: MOD_RES
<222> LOCATION: (5)
<223> OTHER INFORMATION: Xaa = Leu or Met

<400> SEQUENCE: 17

Asp Phe Xaa Asp Xaa Val Ile Trp Gly His Glu His Glu Cys
 1               5                  10

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:consensus
      MRE11 peptide

<400> SEQUENCE: 18

Gln Pro Gly Ser Ser Val
 1               5
```

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence:
    oligonucleotide duplex substrate for MRE11 plate-based assay
<220> FEATURE:
<221> NAME/KEY: modified_base
<222> LOCATION: (1)
<223> OTHER INFORMATION: n = c modified by biotin
<220> FEATURE:
<221> NAME/KEY: modified_base
<222> LOCATION: (27)
<223> OTHER INFORMATION: n = 5-bromo-2'-deoxyuridine
<220> FEATURE:
<221> NAME/KEY: modified_base
<222> LOCATION: (40)
<223> OTHER INFORMATION: n = 5-bromo-2'-deoxyuridine

<400> SEQUENCE: 19
nagccagaca gtggagtact accacbngtg tggcccaggn c                41

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence:
    oligonucleotide duplex substrate for MRE11 plate-based assay

<400> SEQUENCE: 20
gacctgggcc acacagtggt agtactccac tgtctggctg                  40

<210> SEQ ID NO 21
<211> LENGTH: 200
<212> TYPE: PRT
<213> ORGANISM: Artificial Sequence
<220> FEATURE:
<223> OTHER INFORMATION: Description of Artificial Sequence:poly Gly
    flexible linker
<220> FEATURE:
<221> NAME/KEY: MOD_RES
<222> LOCATION: (6)..(200)
<223> OTHER INFORMATION: Gly residues from position 6 to 200 may be
    present or absent

<400> SEQUENCE: 21

Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
 65                 70                  75                  80

Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

-continued

```
Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly
            195                 200
```